US008884101B2

(12) United States Patent
Ishida et al.

(10) Patent No.: US 8,884,101 B2
(45) Date of Patent: Nov. 11, 2014

(54) METHOD OF GENE INTRODUCTION INTO *TRITICUM* PLANT USING *AGROBACTERIUM,* AND A METHOD OF PRODUCING TRANSFORMED *TRITICUM* PLANT

(75) Inventors: Yuji Ishida, Iwata (JP); Yukoh Hiei, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 306 days.

(21) Appl. No.: 13/387,370

(22) PCT Filed: Jul. 29, 2010

(86) PCT No.: PCT/JP2010/062831
§ 371 (c)(1),
(2), (4) Date: Jan. 27, 2012

(87) PCT Pub. No.: WO2011/013764
PCT Pub. Date: Feb. 3, 2011

(65) Prior Publication Data
US 2012/0124696 A1    May 17, 2012

(30) Foreign Application Priority Data

Jul. 29, 2009   (JP) ................................. 2009-176242

(51) Int. Cl.
*A01H 5/10*    (2006.01)
*A01H 1/02*    (2006.01)
*C12N 15/82*   (2006.01)

(52) U.S. Cl.
CPC ................................. *C12N 15/8205* (2013.01)
USPC .......................... 800/294; 800/268; 800/320.3

(58) Field of Classification Search
None
See application file for complete search history.

(56) References Cited

U.S. PATENT DOCUMENTS

| | | | |
|---|---|---|---|
| 7,285,705 B1 | 10/2007 | Risacher et al. | |
| 8,101,820 B2 | 1/2012 | Ishida et al. | |
| 2007/0136898 A1 | 6/2007 | Ishida | |
| 2007/0163007 A1 | 7/2007 | Ishida | |
| 2009/0049567 A1 | 2/2009 | Olhoft et al. | |
| 2011/0131685 A1 | 6/2011 | Ishida et al. | |

FOREIGN PATENT DOCUMENTS

| | | | |
|---|---|---|---|
| CA | 2 290 883 A1 | 12/1998 | |
| JP | 2000-23675 A | 1/2000 | |
| JP | 2002-541853 A | 12/2002 | |
| JP | 2003-199582 A | 7/2003 | |
| JP | 2003-289879 A | 10/2003 | |
| JP | 2008-501327 A | 1/2008 | |
| WO | WO 98/54961 A2 | 12/1998 | |
| WO | WO 00/63398 | * 10/2000 | |
| WO | WO 02/12520 A1 | 2/2002 | |
| WO | WO 02/12521 A1 | 2/2002 | |
| WO | WO 03/007698 A2 | 1/2003 | |
| WO | WO 03/018822 A1 | 3/2003 | |
| WO | WO 2005/017152 A1 | 2/2005 | |
| WO | WO 2005/017169 A1 | 2/2005 | |
| WO | WO 2007/069643 A1 | 6/2007 | |
| WO | WO 2008/105508 A1 | 9/2008 | |
| WO | WO 2008/117887 A1 | 10/2008 | |

OTHER PUBLICATIONS

Wan et al. (Methods in Molecular Biology, vol. 343: *Agrobacterium* Protocols, (2006), Chapter 20, Wheat (*Triticum aestivum* L.), pp. 245-253).*
Hiei et al. (Plant Cell, Tissue and Organ Culture (2006) 85: pp. 271-283).*
Wu et al. (Russian Journal of Plant Physiology, (2006), vol. 53, No. 4, pp. 530-534).*
Hiei (2) et al. (Plant Cell Tiss. Organ Cult., (2006), 87, pp. 233-243).*
Extended European Search Report for Application No. 10804510.5 dated Oct. 24, 2012.
Hu et al., "*Agrobacterium*-mediated large-scale transformation of wheat (*Triticum aestivum* L.) using glyphosate selection", Plant Cell Reports, vol. 21, 2003, pp. 1010-1019, XP003002387.
Sarker et al., "In vitro Plantlet Regeneration and *Agrobacterium*-mediated Genetic Transformation of Wheat (*Triticum aestivum* L.)", Plant Tissue Culture, vol. 12, No. 2, Dec. 2002, pp. 155-165, XP055041055.
Wu et al., "Factors influencing successful *Agrobacterium*-mediated genetic transformation of wheat", Plant Cell Reports, vol. 21, 2003, pp. 659-668, XP055041053.
Cheng et al., "Genetic Transformation of Wheat Mediated by *Agrobacterium tumefaciens*," Plant Physiol. (1997), vol. 115, pp. 971-980.
Cheng et al., "Invited Review: Factors Influencing *Agrobacterium*-Mediated Transformation of Monocotyledonous Species," In Vitro Cell. Dev. Biol.—Plant (Jan.-Feb. 2004), vol. 40, pp. 31-45.
Chu, C.-C. "The N6 medium and its applications to another culture of cereal crops," In: Proc. Symp. Plant Tissue Culture. Peking: Science Press (1978), pp. 43-50.
Datta, K. and S. K. Datta, "Indica Rice (*Oryza sativa*, BR29 and IR64)," Methods in Molecular Biology (2006), vol. 343, *Agrobacterium* Protocols, 2/e, vol. 1, Edited by Kan Wang, Humana Press Inc., Totowa, NJ, pp. 201-212.
De Cleene, M. and J. De Ley, "The Host Range of Crown Gall," The Botanical Review (Oct.-Dec. 1976), vol. 42, No. 4, pp. 389-466.
Frame et al., "*Agrobacterium tumefaciens*-Mediated Transformation of Maize Embryos Using a Standard Binary Vector System," Plant Physiology (May 2002), vol. 129, pp. 13-22.

(Continued)

*Primary Examiner* — Brent T Page
*Assistant Examiner* — Jared Shapiro
(74) *Attorney, Agent, or Firm* — Birch, Stewart, Kolasch & Birch, LLP

(57) ABSTRACT

The method of the present invention includes the step of excising one or more portions selected from a radicle, a germ, and an embryonic axis of a plant tissue inoculated with *Agrobacterium* after cultivation in a coculture medium. The present invention provides a method of gene introduction that can transform a *Triticum* plant at high efficiency compared to conventionally known *Agrobacterium* methods, and provides a method of producing a transformed plant.

11 Claims, 3 Drawing Sheets

(56) References Cited

OTHER PUBLICATIONS

Frame et al., "Maize (*Zea mays* L.)" Methods in Molecular Biology (2006). vol. 343, *Agrobacterium* Protocols, 2/e, vol. 1, Edited by Kan Wang, Humana Press Inc., Totowa, NJ, pp. 185-199.

Gurel et al., "Efficient, reproducible *Agrobacterium*-mediated transformation of *Sorghum* using heat treatment of immature embryos," Plant Cell Rep. (2009), vol. 28, pp. 429-444.

Hiei et al., "Efficient transformation of rice (*Oryza sativa* L.) mediated by *Agrobacterium* and sequence analysis of the boundaries of the T-DNA." The Plant Journal (1994), vol. 6, No. 2, pp. 271-282.

Hiei et al., "Improved frequency of transformation in rice and maize by treatment of immature embryos with centrifugation and heat prior to infection with *Agrobacterium tumefaciens*," Plan Cell Tiss. Organ Cult. (2006), vol. 87, pp. 233-243.

Hiei, Y and T. Komari, "Improved protocols for transformation of indica rice mediated by *Agrobacterium tumefaciens*," Plant Cell, Tissue and Organ Culture (2006), vol. 85, pp. 271-283.

Ishida et al. "*Agrobacterium*-mediated transformation of maize," Nature Protocols (2007), vol. 2, No. 7, pp. 1614-1621.

Ishida et al.. "High efficiency transformation of maize (*Zea mays* L.) mediated by *Agrobacterium tumefaciens*," Nature Biotechnology (Jun. 1996), vol. 14, pp. 745-750.

Ishida et al., "Improved Protocol for Transformation of Maize (*Zea mays* L.) Mediated by *Agrobacterium tumefaciens*," Plant Biotechnology (2003) vol. 20, No. 1, pp. 57-66.

Jacobsen et al., "Barley (*Hordeum vulgare* L.)," Methods in Molecular Biology (2006), vol. 343, *Agrobacterium* protocols, 2/e, vol. 1, Edited by Kan Wang, Humana Pres Inc., Totowa, NJ, pp. 171-183.

Jones et al., "Review of methodologies and a protocol for the *Agrobacterium*-mediaed transformation of wheat," Plant Methods (Sep. 5, 2005), vol. 1, No. 5.

Ke et al., "Manipulation of discriminatory T-DNA delivery by *Agrobacterium* into cells of immature embryos of barley and wheat," Euphytica (2002), vol. 126, pp. 333-343.

Khanna, H. K. and G. E. Daggard, "*Agrobacterium tumefaciens*-mediated transformation of wheat using a superbinary vector and a polymine-supplemented regeneration medium." Plant Cell. Rep. (2003), vol. 21, pp. 429-436.

Komari et al., "Efficient selection of somatic hybrids in *Nicotiana tabacum* L. using a combination of drug-resistant markers introduced by transformation," Theor. Appl. Genet. (1989), vol. 77, pp. 547-552.

Linsmaier, E. M. and F. Skoog, "Organic Growth Factor Requirements of Tobacco Tissue Cultures," Physiologia Plantarum (1965), vol. 18, pp. 100-127.

Negrotto et al., "The use of phosphomannose-isomerase as a selectable marker to recover transgenic maize plants (*Zea meys* L.) via *Agrobacterium* transformation," Plant Cell Reports (2000), vol. 19, pp. 798-803.

Potrykus, I., "Gene Transfer to Cereals: An Assessment," Bio/Technology (Jun. 1990), vol. 8, pp. 535-542.

Przetakiewicz et al., "*Agrobacterium*-Mediated Transformation of Polyploid Cereals. The Efficiency of Selection and Transgene Expression in Wheat," Cellular & Molecular Biology Letters (2004), vol. 9, pp. 903-917.

Risacher et al., "Highly Efficient *Agrobacterium*-Mediated Transformation of Wheat Via *In Planta* Inoculation," Methods in Molecular Biology. Transgenic Wheat, Barley and Oats (2009), vol. 478, Huw D. Jones and Peter R. Shewry (eds.), Humana Press, pp. 115-124.

Shrawat et al., "*Agrobacterium tumefaciens*-mediated genetic transformation of barley (*Hordsum vulgare* L.)," Plant Science (2007), vol. 172, pp. 281-290.

Tingay et al., "*Agrobacterium tumefaciens*-mediated barley transformation." The Plant Journal (1997), vol. 11, No. 6, pp. 1369-1376.

Wan, Y. and J. Layton, Wheat (*Triticum aestivum* L.), Methods in Molecular Biology (2006), vol. 343, *Agrobacterium* Protocols, 2/e, vol. 1, Edited by Kan Wang, Humana Press Inc., Totwa, NJ pp. 245-253.

Wang et al., "Transgenic Wheat Plants Derived from *Agrobacterium*-mediated Transformation of Mature Embryo Tissues," Cereal Res. Comm. (2009), vol. 37, No. 1, pp. 1-12.

Wang, K., "Preface," Methods in Molecular Biology (2006), vol. 343, *Agrobacterium* Protocols, 2/e, vol. 1, Edited by Kan Wang, Humana Press Inc.. Totowa, NJ, pp. vii-viii.

Watson et al., "Plasmid Required for Virulence of *Agrobacterium tumefaciens*." Journal of Bacteriology (Jul. 1975), vol. 123, No. 1, pp. 255-264.

Wu et al., "Efficient and rapid *Agrobacterium*-mediated genetic transformation of *durum* wheat (*Triticum turgidum* L. var. *durum*) using additional virulence genes," Transgenic Research (2008), vol. 17, pp. 425-436.

Zhao et al., "*Agrobacterium*-mediated *Sorghum* transformation," Plant Molecular Biology (2000), vol. 44, pp. 789-798.

Zhao et al., "High throughout genetic transformation mediated by *Agrobacterium tumefaciens* in maize," Molecular Breeding (2001), vol. 8, pp. 323-333.

\* cited by examiner

SEQUENCE LISTING

<160> NUMBER OF SEQ ID NOS: 6

<210> SEQ ID NO 1
<211> LENGTH: 37
<212> TYPE: DNA
<213> ORGANISM: Artificial Sequence
<220> FEATURE:
<223> OTHER INFORMATION: primer BglII-Icat_Fw

<400> SEQUENCE: 1 actctagaaac atagatctct acagggtaaa tttctag       37

<210> SEQ ID NO 2
<211> LENGTH: 43
<212> TYPE: DNA
<213> ORGANISM: Artificial Sequence
<220> FEATURE:
<223> OTHER INFORMATION: primer BamHI-GNos_Rv

<400> SEQUENCE: 2
tttggatccg cgtcgacgcg tcgacgcgtc ctagaagcta att       43

<210> SEQ ID NO 3
<211> LENGTH: 37
<212> TYPE: DNA
<213> ORGANISM: Artificial Sequence
<220> FEATURE:
<223> OTHER INFORMATION: primer BamHI-Pubi_Fw

<400> SEQUENCE: 3 actctagaaac atagatctct acagggtaaa tttctag       37

<210> SEQ ID NO 4
<211> LENGTH: 46
<212> TYPE: DNA
<213> ORGANISM: Artificial Sequence
<220> FEATURE:
<223> OTHER INFORMATION: primer Bar-Iubi_Rv

<400> SEQUENCE: 4
tcgttctggg tccatatctc attgcccccc gggatgctct agagtc       46

<210> SEQ ID NO 5
<211> LENGTH: 45
<212> TYPE: DNA
<213> ORGANISM: Artificial Sequence
<220> FEATURE:
<223> OTHER INFORMATION: primer Iubi-Bar_Fw

<400> SEQUENCE: 5

```
gggggcaat gagatatgga cccagaacga cgcccggccg acatc                45
```

<210> SEQ ID NO 6
<211> LENGTH: 44
<212> TYPE: DNA
<213> ORGANISM: Artificial Sequence
<220> FEATURE:
<223> OTHER INFORMATION: primer pIG121-Bar_Rv

<400> SEQUENCE: 6

```
ctttggatcc cggtcggcta ctactctcag atctcggtga cggg                 44
```

METHOD OF GENE INTRODUCTION INTO *TRITICUM* PLANT USING *AGROBACTERIUM*, AND A METHOD OF PRODUCING TRANSFORMED *TRITICUM* PLANT

TECHNICAL FIELD

The present invention relates to a method of gene introduction into a *Triticum* plant via *Agrobacterium*. The present invention also relates to a method of producing a transformed *Triticum* plant via *Agrobacterium*.

BACKGROUND ART

Several methods, for example, an electroporation method and a particle gun method are known for transforming monocotyledons such as wheat, corn, and rice, which are major grain crops. However, these physical gene introduction methods have disadvantages in that a gene is introduced as multiple copies or is not inserted in an intact state, and the resulting transformed plant may often develop a malformation and sterility.

Gene introduction mediated by *Agrobacterium* is generally used for transformation of dicotyledons. Although it has been understood that hosts of *Agrobacterium* are limited only to dicotyledons and *Agrobacterium* have no ability to infect monocotyledons (NPL 1), some attempts have been made to transform monocotyledons through *Agrobacterium*.

In 1990, there were research reports suggesting that gene introduction can also be mediated by *Agrobacterium* in Gramineae crops such as rice, corn, and wheat. However, these reports failed to show persuasive results because these studies had a problem in reproducibility and were also insufficient for confirmation of introduced genes (NPL 2).

Improvement in *Agrobacterium* Method

Recent reports involve that monocotyledons such as rice and corn can also be stably and efficiently transformed using super-binary vectors carrying parts of virulence genes of super-virulent *Agrobacterium* (NPLs 3 and 4). These reports state that transformation mediated by *Agrobacterium* has, in addition to stable and highly efficient transformation, advantages in that the resulting transformed plants have fewer mutations and that the introduced genes are low in copy number and are often in the intact states. Following the success in rice and corn, further reports were issued for *Agrobacterium*-mediated transformation in, for example, barley (NPL 6) and sorghum (NPL 7).

Ishida et al. (1996) (NPL 4) performed *Agrobacterium*-mediated transformation using a corn inbred line as a material. Furthermore, *Agrobacterium*-mediated transformation of corn has been reported (NPLs 8 to 10). Improvements have been attempted in the efficiency in *Agrobacterium*-mediated transformation of corn: for example, selection of transformed cells by means of an N6 basal medium (NPL 9), addition of $AgNO_3$ and carbenicillin to a medium (NPLs 9 and 11), and addition of cysteine to a coculture medium (NPL 10). Ishida et al. (2003) (NPL 11) have reported that the transformation efficiency in corn is improved by selecting cocultured immature corn embryos by means of a medium containing $AgNO_3$ and carbenicillin.

Hiei et al. (2006) (NPL 12) have reported that thermal and/or centrifugation treatment(s) of immature embryos prior to inoculation with *Agrobacterium* enhances the transformation efficiencies of rice and corn and also enables of transforming varieties that have not been transformed before. Hiei and Komari (2006) (NPL 13) have reported that the transformation efficiency of Indica rice is enhanced by modifying the composition and gelling agent of a coculture medium.

Thus, the modifications in medium composition and selection marker gene and the pretreatment of a plant tissue slice as a material notably enhance the efficiency in *Agrobacterium*-mediated transformation of rice and corn, compared to the initially reported efficiency, and such modification and pretreatment have extended the range of varieties to be applied.

Use of Immature Embryo

As materials for *Agrobacterium*-mediated transformation of monocotyledonous crops, immature embryos and immature embryos cultured for a short period of time are most appropriate, and immature embryos of crops such as corn, wheat, and barley are main targets of *Agrobacterium* infection (Cheng et al., (2004): NPL 14).

In corn and sorghum among major grain crops, immature embryos immediately after isolation are inoculated with *Agrobacterium* and are cocultured, and then transformed cells and transformed plants are selected (Frame et al., (2006): NPL 15, Ishida et al., (2007): NPL 16, Zhao et al., (2000): NPL 7, Gurel et al., (2009): NPL 17).

In transformation of rice using the immature embryo immediately after isolation as a material, the embryonic axis is excised from the immature embryo that has been inoculated with *Agrobacterium* and cocultured. The embryonic axis is removed after the coculture for removing extended bud and root (Hiei and Komari (2006): NPL 13, Datta and Datta (2006): NPL 18).

In barley, the embryonic axis is excised from the immature embryo or is wounded prior to inoculation with *Agrobacterium*, and then transformation mediated by *Agrobacterium* is performed (Tingay et al., (1997): NPL 6, Sharawat et al., (2007): NPL 19). It is difficult to remove the embryonic axis from an isolated barley immature embryo; hence constant preparation of a satisfactory immature embryo requires training for several days (Jacobsen et al., (2006): NPL 20). This troublesome process is conducted for increasing the rate of callus formation from immature embryos (Sharawat et al., (2007): NPL 19).

Thus, in the case of an immature embryo used as a material for transformation of the above-described grain crops, it is clearly determined whether or not the embryonic axis is removed from the immature embryo and when the removal is performed in the case where the embryonic axis is removed, depending on the type of the crop.

It has been also reported on attempts of producing a transformed plant of wheat, which is one of the main grain crops, mediated by *Agrobacterium* using the immature embryo.

For example, Cheng et al. (1997) (NPL 5) have reported that transformants can be obtained at an efficiency of 0.14% to 4.3% by inoculating immature embryos, precultured immature embryos, and calluses derived from immature embryos of wheat (variety: Bobwhite) with *Agrobacterium* and selecting transformed cells and plants by means of a medium containing G418. Furthermore, production of transformed wheat through *Agrobacterium* has been reported, but even today, more than ten years have passed from the first report by Cheng et al. (1997) (NPL 5), the efficiency is less than 5% in most reports, and the varieties to be applied are limited. Additional disadvantages, for example, low reproducibility of the published results, large variations in experimental results, and limited time for obtaining a satisfactory plant material.

Reports on wheat where immature embryos are used as a material lack in consistency; that is, many reports do not mention the process of excising embryonic axes, while some reports mention removal of embryonic axes (Przetakiewicz et al., (2004): NPL 21, Jones et al., (2005): NPL 22, Wan and Layton (2006): NPL 23, Wu et al., (2008): NPL 24, Khanna and Daggard (2003): NPL 25). Among these reports, in the reports mentioning removal of the embryonic axes in transformation of wheat, the embryonic axes are excised from the immature embryos before inoculation with *Agrobacterium*.

Furthermore, regarding excision of the embryonic axis of a wheat immature embryo as a material for transformation, Jones et al. (2005) states that "precocious zygotic germination is a significant problem when immature embryo explants are used but can be suppressed by the addition of plant hormones such as dicamba, abscisic acid, or high levels of 2,4-D to the culture medium in the literature (NPL 22). Some authors specifically state that the embryonic axis was removed or damaged to prevent zygotic germination". It is comprehended from the description above that when immature embryo is used in transformation of wheat, the problem of immature embryo germination is solved using plant hormones, and in particular, treatment of embryonic axis is unnecessary.

In addition, it is disclosed that the target tissue (embryo) of an immature wheat seed is inoculated with *Agrobacterium* at the time when the plant is present in its natural plant environment and is cocultured with the *Agrobacterium* and then that a transformed plant is obtained through dedifferentiation and regeneration of the target tissue. These literatures describe embryonic axis treatment of wheat immature embryos (PCT Japanese Translation Patent Publication No. 2002-541853 (PTL 1), Risacher et al., (2009): NPL 33). In PTL 1, the embryonic axis is removed after inoculation and coculture with *Agrobacterium*, but in the NPL, the embryonic axis is removed after evaluation of β-glucuronidase (GUS) expression. This means that the embryonic axis is removed after gene introduction. In addition, in the technology disclosed in PTL 1, inoculation with *Agrobacterium* is performed in the natural plant environment, that is, in the state where the embryo of an immature wheat seed is attached to the plant.

In NPL 33, an immature wheat seed of which target tissue (embryo) has a size of about 1 mm is inoculated with *Agrobacterium* by the method described in PTL 1, and the immature seed is stored as an ear for two to three days. Then, the immature embryo is isolated from the seed and is placed onto a medium containing an antibiotic for sterilizing *Agrobacterium*, followed by cultivation for 5 days. Subsequently, the embryonic axis is excised from the immature embryo after the cultivation, and the embryo is cultured in the same medium for 7 days, followed by selection and regeneration of the transformed cell.

As described above, in *Agrobacterium*-mediated transformation of wheat, transformed plants can be obtained by the known methods. However, the transformation efficiency is significantly low compared to those in rice and corn, which are the same monocotyledons as wheat, and has a problem in experimental reproducibility. Accordingly, there is a demand for developing a method capable of producing a transformant with higher efficiency and reproducibility. In addition, there are various reports on the time when the embryonic axis is removed in wheat, and a fixed knowledge has not been established yet.

CITATION LIST

Patent Literature

PTL 1: PCT Japanese Translation Patent Publication No. 2002-541853
PTL 2: WO1998/054961
PTL 3: WO2002/012520
PTL 4: Japanese Unexamined Patent Application Publication No. 2000-023675
PTL 5: WO2002/012521
PTL 6: WO2005/017169
PTL 7: WO2005/017152
PTL 8: WO2007/069643

Non Patent Literature

NPL 1: De Cleene, M. and De Ley, J., (1976) The host range of crown gall, Bot. Rev., 42: 389-466
NPL 2: Potrycus, I (1990) Gene transfer to cereals: an assessment. Bio/technology 8:535-542
NPL 3: Hiei, Y., Ohta, S., Komari, T., and Kumashiro, T., (1994) Efficient transformation of rice (*Oryza sativa* L.) mediated by *Agrobacterium* and sequence analysis of the boundaries of the T-DNA, The Plant Journal, 6: 271-282
NPL 4: Ishida, Y., Saito, H., Ohta, S., Hiei, Y., Komari, T., and Kumashiro, T., (1996) High efficiency transformation of maize (*Zea mays* L.) mediated by *Agrobacterium tumefaciens*, Nature Biotechnology, 14: 745-750
NPL 5: Cheng, M., Fry, J. E., Pang, S., Zhou, H., Hironaka, C. M., Duncan, D. R., Conner, T. W., and Wan, Y., (1997) Genetic transformation of wheat mediated by *Agrobacterium tumefaciens*, Plant Physiol., 115: 971-980
NPL 6: Tingay, S., McElroy, D., Kalla, R., Fieg, S., Wang, M., Thornton, and S., Brettell, R., (1997) *Agrobacterium tumefaciens*-mediated barley transformation, Plant J., 11: 1369-1376
NPL 7: Zhao, Z.-Y., Cai, T., Tagliani, L., Miller, M., Wang, N., Peng, H., Rudert, M., Schoeder, S., Hondred, D., Seltzer, J., and Pierce, D., (2000) *Agrobacterium*-mediated sorghum transformation, Plant Mol. Biol., 44: 789-798
NPL 8: Negrotto, D., Jolley, M., Beer, S., Wenck, A. R., and Hansen, G., (2000) The use of phosphomannose-isomerase as a selection marker to recover transgenic maize plants (*Zea mays* L.) via *Agrobacterium* transformation, Plant Cell Reports, 19: 798-803
NPL 9: Zhao, Z.-Y., Gu, W., Cai, T., Tagliani, L., Hondred, D., Bond, D., Schroeder, S., Rudert, M., and Pierce, D., (2001) High throughput genetic transformation mediated by *Agrobacterium tumefaciens* in maize, Mol. Breed., 8: 323-333
NPL 10: Frame, B. R., Shou, H., Chikwamba, R. K., Zhang, Z., Xiang, C., Fonger, T. M., Pegg, S. E. K., Li, B., Nettleton, D. S., Pei, D., and Wang, K. (2002) *Agrobacterium tumefaciens*-mediated transformation of maize embryos using a standard binary vector system, Plant Physiol., 129: 13-22
NPL 11: Ishida, Y., Saito, H., Hiei, Y., and Komari, T. (2003) Improved protocol for transformation of maize (*Zea mays* L.) mediated by *Agrobacterium tumefaciens*, Plant Biotechnology, 20: 57-66
NPL 12: Hiei, Y., Ishida, Y., Kasaoka, K., and Komari, T., (2006) Improved frequency of transformation of rice and maize by treatment of immature embryos with centrifugation and heat prior to infection with *Agrobacterium tumefaciens*, Plant Cell Tissue and Organ Culture, 87: 233-243
NPL 13: Hiei, Y. and Komari, T., (2006) Improved protocol for transformation of Indica rice mediated by *Agrobacterium tumefaciens*, Plant Cell Tissue and Organ Culture, 85: 271-283
NPL 14: Cheng, et al., (2004) Invited revier: Factors influencing *Agrobacterium*-mediated transformation of monocotyledonous species, In Vitro Cell. Dev. Biol. Plant, 40: 31-45

NPL 15: Frame, et al., (2006) Maize (*Zea mays* L.) Methods in Molecular Biology, vol. 343, *Agrobacterium* protocols, volume 1, Edited by Kan Wang, Humana Press Inc., Totowa, N.J., pp. 185-199
NPL 16: Ishida, et al., (2007) *Agrobacterium*-mediated transformation of maize, Nature Protocols, 2: 1614-1621
NPL 17: Gurel, et al., (2009) Efficient, reproducible *Agrobacterium*-mediated transformation of sorghum using heat treatment of immature embryos, Plant Cell Reports, 28: 429-444
NPL 18: Datta and Datta (2006) Indica Rice (*Oryza sativa*, BR29 and IR64) Methods in Molecular Biology, vol. 343, *Agrobacterium* protocols, volume 1, Edited by Kan Wang, Humana Press Inc., Totowa, N.J., pp. 201-212
NPL 19: Sharawat, et al., (2007) *Agrobacterium tumefaciens*-mediated genetic transformation of barley (*Hordeum vulgare* L.), Plant Science, 172: 281-290
NPL 20: Jacobsen, et al., (2006) Barley (*Hordeum vulgare* L.) Methods in Molecular Biology, vol. 343, *Agrobacterium* protocols, volume 1, Edited by Kan Wang, Humana Press Inc., Totowa, N.J., pp. 171-183
NPL 21: Przetakiewicz, et al., (2004) *Agrobacterium*-mediated transformation of polyploid cereals, The efficiency of selection and transgene expression in wheat, Cellular & Molecular Biology Letters, 9: 903-917
NPL 22: Jones, et al., (2005) Review of methodologies and a protocol for the *Agrobacterium*-mediated transformation of wheat, Plant Methods, 1: 5
NPL 23: Wan and Layton, (2006) Wheat (*Triticum aestivums* L.) Methods in Molecular Biology, vol. 343, *Agrobacterium* protocols, volume 1, Edited by Kan Wang, Humana Press Inc., Totowa, N.J., pp. 245-253
NPL 24: Wu, et al., (2008) Efficient and rapid *Agrobacterium*-mediated genetic transformation of durum wheat (*Triticum turgidum* L. var. *durum*) using additional virulence genes, Transgenic Research, 17: 425-436
NPL 25: Khanna and Daggard, (2003) *Agrobacterium tumefaciens*-mediated transformation of wheat using a superbinary vector and a polyamine-supplemented regeneration medium, Plant Cell Reports, 21: 429-436
NPL 26: Sambrook, J., Fritsch, E. F., and Maniatis, T., (2001) Molecular Cloning: A Laboratory Manual, 3rd ed., Cold Spring Harbor Laboratory Press, Cold Spring Harbor, N.Y.
NPL 27: Linsmaier, E. and Skoog, F. (1965) Organic growth factor requirements of tobacco tissue culture, Physiol. Plant, 18: 100-127
NPL 28: Chu, C.-C. (1978), The N6 medium and its applications to another culture of cereal crops. In: Proc. Symp. Plant Tissue Culture. Peking: Science Press, pp. 43-50
NPL 29: Komari, et al., (1989) Efficient selection of somatic hybrids in *Nicotiana tabacum* L. using a combination of drug-resistance markers introduced by transformation, Theor. Appl. Genet., 77: 547-552
NPL 30: Ke, et al., (2002) Manipulation of discriminatory T-DNA delivery by *Agrobacterium* into cells of immature embryos of barley and wheat, Euphytica, 126: 333-343
NPL 31: Watson, et al., (1975) Plasmid required for virulence of *Agrobacterium tumefaciens*, J. Bacteriol., 123: 255-264
NPL 32: Kan Wang, (2006) Preface Methods in Molecular Biology, vol. 343, *Agrobacterium* protocols, volume 1, Edited by Kan Wang, Humana Press Inc., Totowa, N.J., vii-viii.
NPL 33: Risacher, et al., (2009) Highly Efficient *Agrobacterium*-Mediated Transformation of Wheat Via In Planta Inoculation, Method in Molecular Biology, Transgenic Wheat, Barley and Oats, vol. 478, Humana Press, pp. 115-124
NPL 34: Jones, et al., (2005) Review of methodologies and a protocol for the *Agrobacterium*-mediated transformation of wheat, Plant Methods I: 5

SUMMARY OF INVENTION

Technical Problem

It is an object of the present invention to provide a method of gene introduction into a *Triticum* plant for transformation at a higher efficiency compared to that in known *Agrobacterium* methods, and a method of producing a transformed *Triticum* plant.

Solution to Problem

The present inventors have diligently studied in order to solve the foregoing problems and, as a result, have found that the transformation efficiency of a *Triticum* plant is enhanced, compared to those of conventional methods, by physically and/or chemically damaging one or more portions selected from a radicle, a germ, and an embryonic axis simultaneous with and/or subsequent to coculture step of culturing a tissue of an immature embryo or mature seed of a *Triticum* plant inoculated with *Agrobacterium* in a coculture medium, and have arrived at the present invention.

The present invention is preferably accomplished by the embodiments described below, but is not limited thereto.

Embodiment 1

A method of gene introduction into a tissue of an immature embryo or mature seed of a *Triticum* plant, including the steps of:
(i) coculture step by coculturing the tissue inoculated with *Agrobacterium*, in the presence of the *Agrobacterium*; and
(ii) a step of physically and/or chemically damaging one or more portions selected from a radicle, a germ, and an embryonic axis of the tissue simultaneous with and/or subsequent to the coculture step.

Embodiment 2

A method of producing a transformed *Triticum* plant, including the steps of:
(i) coculture step by coculturing a tissue of an immature embryo or mature seed inoculated with *Agrobacterium*, in the presence of the *Agrobacterium*;
(ii) a step of physically and/or chemically damaging one or more portions selected from a radicle, a germ, and an embryonic axis of the tissue simultaneous with and/or subsequent to the coculture step;
(iii) resting step by culturing the tissue on a resting medium; and
(iv) regeneration step by regenerating the tissue on a regeneration medium.

Embodiment 3

The method according to Embodiment 1 or 2, wherein the step of physically and/or chemically damaging one or more portions selected from a radicle, a germ, and an embryonic axis of the tissue comprises excising one or more portions selected from the radicle, the germ, and the embryonic axis from the tissue.

Embodiment 4

The method according to any one of Embodiments 1 to 3, wherein the step of physically and/or chemically damaging one or more portions selected from a radicle, a germ, and an embryonic axis of the tissue is performed simultaneous with the coculture step and/or within seven days from the beginning of the coculture step.

Embodiment 5

The method according to any one of Embodiments 1 to 3, wherein the step of physically and/or chemically damaging one or more portions selected from a radicle, a germ, and an embryonic axis of the tissue is performed within one to three days from the beginning of the coculture step.

Embodiment 6

The method according to any one of Embodiments 1 to 5, wherein the coculture medium does not contain a plant growth regulator.

Embodiment 7

The method according to any one of Embodiments 1 to 6, the method further including at least one treatment for transformation efficiency enhancement selected from the group consisting of:
a) centrifugation;
b) addition of silver nitrate and/or copper sulfate to the coculture medium;
c) thermal treatment;
d) thermal treatment and centrifugation;
e) pressurization;
f) inoculation with *Agrobacterium* in the presence of a powder; and
g) addition of cysteine to the coculture medium.

Embodiment 8

The method according to any one of Embodiment 1 to 6, the method further including the following a) and/or b) treatment for transformation efficiency enhancement:
a) centrifugation;
b) addition of silver nitrate and/or copper sulfate to the coculture medium.

Embodiment 9

The method according to any one of Embodiments 2 to 8, the method further comprising a step of selection with a selective drug between the resting step (iii) and the regeneration step (iv).

Embodiment 10

The method according to any one of Embodiments 2 to 9, wherein the resting medium (iii) and/or a selection medium for the step of selection with a selective drug contains a plant growth regulator.

Embodiment 11

The method according to any one of Embodiments 1 to 10, wherein the *Agrobacterium* is a bacterium selected from the group consisting of LBA4404, EHA101, EHA105, AGL1C, and 58C1.

Embodiment 12

The method according to any one of Embodiments 1 to 11, wherein the *Triticum* plant is bread wheat (*Triticum aestivum*) or macaroni wheat (*Triticum durum*).

Advantageous Effects of Invention

The present invention enables a *Triticum* plant to be transformed with a high efficiency. Accordingly, a stably transformed plant can be obtained with high reproducibility, resulting in reduced costs for obtaining the plant.

BRIEF DESCRIPTION OF DRAWINGS

In FIG. 3, the group A represents a test group where immature embryos were subjected to centrifugation at 15000 rpm for 10 min before inoculation with *Agrobacterium*, the group B represents a test group where immature embryos were subjected to inoculation with *Agrobacterium* and excision of radicles, genus, and embryonic axes and then centrifugation at 15000 rpm for 10 min, and the group C represents a test group where immature embryos were subjected to inoculation with *Agrobacterium*, centrifugation at 15000 rpm for 10 min, and then excision of radicles, germs, and embryonic axes. The immature embryos were evaluated by expression of a GUS gene in individual immature embryos cultured in a resting medium for five days in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression). In each group, the evaluation was performed with 19 to 25 immature embryos, and the average value thereof was plotted on the vertical axis of FIG. 3. That is, the vertical axis in FIG. 3 represents efficiencies of gene introduction evaluated by expression of the GUS gene.

DESCRIPTION OF EMBODIMENTS

Figure 1:
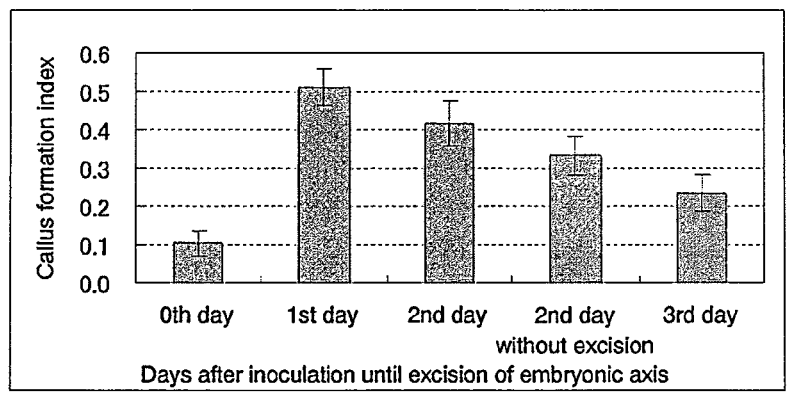
FIG. 1 is a graph showing the effect of excision of a radicle, a germ, and an embryonic axis on callus formation from wheat immature embryos inoculated with *Agrobacterium*. In each test group, 36 to 43 immature embryos were used. In the experiments shown in FIG. 1, the wheat immature embryos were placed onto a coculture medium after inoculation with *Agrobacterium* until excision of the radicle, germ, and embryonic axis. The vertical axis represents the index of callus formation from immature embryos, while the horizontal axis represents days from inoculation with *Agrobacterium* to placement of immature embryos after excision of the radicles, germs, and embryonic axes onto a resting medium. The index of callus formation is a value for evaluating individual immature embryos on the ninth day from the inoculation in three grades: 1 (callus formation occurring in a half or more of scutellum), 0.5 (callus formation occurring in a part of scutellum), and 0 (no callus formation occurring). The "0th day" on the horizontal axis represents immature embryos from which the embryonic axes were excised before inoculation with *Agrobacterium*. The "2nd day without excision" represents immature embryos placed onto a resting medium on the 2nd day from the inoculation with *Agrobacterium* without excision of the embryonic axes.

The constitution of the present invention will now be described in detail.

The present invention provides a method of gene introduction into a tissue of an immature embryo or mature seed of a *Triticum* plant, comprising the steps of:

(i) coculture step by coculturing the tissue inoculated with *Agrobacterium*, in the presence of the *Agrobacterium*; and (ii) a step of physically and/or chemically damaging one or more portions selected from a radicle, a germ, and an embryonic axis of the tissue simultaneously with and/or subsequent to the coculture step.

The present invention further provides a method of producing a transformed *Triticum* plant, comprising the steps of:

(i) coculture step by coculturing a tissue of an immature embryo or mature seed inoculated with *Agrobacterium*, in the presence of the *Agrobacterium*;

(ii) a step of physically and/or chemically damaging one or more portions selected from a radicle, a germ, and an embryonic axis of the tissue simultaneously with and/or subsequent to the coculture step;

(iii) resting step by culturing the tissue on a resting medium; and (iv) regeneration step by regenerating the tissue on a regeneration medium.

The plant from which the plant tissues usable in the present invention derive is a *Triticum* plant. Examples of the "*Triticum*" plant in this specification include, but not limited to, wheats of a one-grain system, i.e., *T. aegilopoides*, *T. thaoudar*, and *T. monococcum* (einkorn); wheats of a two-grain system, i.e., *T. dicoccoides*, *T. dicoccum* (emmer wheat), *T. pyromidale*, *T. orientale* (khorasan wheat), *T. durum* (durum wheat, macaroni wheat), *T. turgidum* (rivet wheat), *T. polonicum* (poulard wheat), and *T. persicum* (persian wheat); and wheats of a three-grain system, i.e., *T. aestivum* (common wheat, bread wheat), *T. spelta* (spelt wheat), *T. compactum* (club wheat, compact ear wheat), *T. sphaerococcum* (Indian dwarf wheat), *T. maha* (macha wheat), and *T. vavilovii* (vavilovi wheat). In the present invention, bread wheat (*T. aestivum*) and macaroni wheat (*T. durum*) are preferred, and bread wheat (*T. aestivum*) is particularly preferred.

The plant tissues usable in the present invention are immature embryos and mature seeds, preferably immature embryos. Throughout the specification, the term "immature embryo" refers to an embryo of an immature seed during maturation after pollination. Any stage (maturing stage) of an immature embryo can be used in the method of the present invention without limitation, and the immature embryo may be harvested at any stage after pollination, and preferably on 7th to 21st day from pollination. Throughout the specification, the term "mature seed" refers to a fully-ripened seed after completion of maturation after pollination.

Each process mentioned above will be described in detail below.

1. Individual Steps of the Present Invention

The method of gene introduction and the method of producing a transformed plant of the present invention utilize *Agrobacterium*. These methods can be conducted in accordance with individual steps in known methods of gene introduction and transformation using *Agrobacterium*, unless mentioned otherwise.

(1) The Coculture Step

In the present invention, coculture is performed where a tissue of an immature embryo or mature seed inoculated with an *Agrobacterium* is cultured in the presence of the *Agrobacterium*. This step involves cultivation of the plant tissue inoculated with the *Agrobacterium* in the presence of the *Agrobacterium* in order to ensure introduction of DNA from the *Agrobacterium* into plant cells.

The method of gene introduction or the method of producing a transformed plant of the present invention preferably uses tissue isolated/harvested from a plant body of a plant belonging to the genus *Triticum*. Accordingly, in the present invention, a tissue (immature embryo or mature seed) is isolated/harvested from the plant body of a plant belonging to the genus *Triticum*, and the isolated/harvested tissue is then inoculated with an *Agrobacterium*.

In the present invention, the size of the plant tissue to be used, which is an immature embryo, is not particularly limited. For example, the size of the wheat immature embryo used in NPL 33 is 1 mm, and Jones et al. (2005) (NPL 34) describe that the size of the immature embryo used for transformation of wheat must be 0.8 to 1.5 mm.

The present inventors have found that the transformation efficiency in wheat is further enhanced if an embryo has a size of certain level or more (Example 10). Accordingly, the wheat immature embryo to be used in the present invention preferably has a size of certain level or more. The size of a wheat immature embryo at the time it is inoculated with *Agrobacterium* is, but not limited to, preferably 1.2 mm or more, more preferably larger than 1.5 mm, and most preferably 2.2 mm or more.

The upper limit of the size of a wheat immature embryo used in the present invention is not limited and may correspond to the largest one obtained from the *Triticum* plant as a target for gene introduction. For example, an immature embryo of the variety Fielder, which usually a maximum size of about 3.0 mm, can also be suitably used.

The above-described plant tissue may be subjected to various treatments for enhancing transformation efficiency. Examples of the treatment include thermal treatment (PTL 2), centrifugation (PTL 3), thermal treatment and centrifugation (PTL 5), and pressurization (PTL 6). These treatments may be employed before inoculation with *Agrobacterium*, simultaneous with inoculation with *Agrobacterium*, or after inoculation with *Agrobacterium*. The treatments for enhancing transformation efficiency will be described in detail below.

In the present invention, a tissue of a *Triticum* plant is inoculated with *Agrobacterium*.

Throughout the specification, the term "inoculation" refers to bringing *Agrobacterium* into contact with a tissue (e.g., scutelum) of a plant, and various methods for inoculation with *Agrobacterium* are known in the art. Examples of the method include a method where a plant tissue is added to suspension of *Agrobacterium* in a liquid medium, a method where suspension of *Agrobacterium* is directly dropped onto a plant tissue in a coculture medium, a method where suspension of *Agrobacterium* is injected into a plant tissue, and a method where a plant tissue is immersed in suspension of *Agrobacterium* with a reduced pressure. However, the method of inoculation with *Agrobacterium* in the present invention is not limited to these methods.

In the inoculation with *Agrobacterium*, in order to enhance the transformation efficiency by the *Agrobacterium*, for example, various additives such as acetosyringone, a surfactant, or a porous ceramic may be added to the suspension of the *Agrobacterium*.

Any known *Agrobacterium* can be used in transformation by *Agrobacterium* without limitation in the present invention. In a preferred embodiment of the present invention, the *Agrobacterium* is, for example, LBA4404, EHA101, EHA105, AGL1, or C58C1, but is not limited thereto. If super-binary vectors (NPLs 3 and 4) are not used, a bacterial strain containing Ti plasmid pTiBo542 possessed by *Agrobacterium* A281 (NPL 31) is preferably used from the viewpoint of transformation efficiency.

It is known that *Agrobacterium* has a property of introducing a gene inserted in T-DNA of a plasmid in *Agrobacterium* into the genome of a plant. Thus, *Agrobacterium* usable in the present invention has a plasmid T-DNA into which a gene to be expressed by a plant is inserted. A plant can be transformed through inoculation of a tissue of the plant with *Agrobacterium* having this plasmid. A desired characteristic can thereby be provided to the plant cells in the tissue. Examples of the plasmid for *Agrobacterium* usable in the present invention include, but not limited to, pSB131, U0009B, U0017S, pSB134, pNB131, and pIG121Hm.

The medium used in this step is referred to as "coculture medium" throughout the specification. The coculture medium may be any medium that is usually used for cultivation of plant cells, and examples thereof include medium based on LS inorganic salts (NPL 27) or N6 inorganic salts (NPL 28). Preferred examples of the medium include, but not limited to, medium containing reduced amounts of inorganic salts and/or vitamins that are usually contained in medium used for tissue culture as described above. The amounts are reduced more preferably to one-fifth or less, most preferably to one-tenth or less, and specifically, an MS medium with a concentration of one-tenth can be suitably used.

Ke et al. (2002) (NPL 30) discloses an example of a coculture medium not containing a plant growth regulator which is used for cultivation of barley.

The coculture medium in the present invention may contain, for example, but not limited to, an auxin such as 2,4-dichlorophenoxyacetic acid (2,4-D), picloram, or another auxin; a cytokinin such as kinetin or 4PU; or another plant growth regulator.

The present inventors have further found that a lower concentration of the auxin in a coculture medium enhances the transformation efficiency, as shown in Examples 1 and 9 below. Accordingly, the concentration of auxin contained in the coculture medium in the present invention is not particularly limited, which is preferably 5 µM or less, more preferably 0.5 µM or less, and in the most preferable embodiment, the auxin is not contained at all.

In order to further enhance transformation efficiency, the coculture medium may contain various additives. Examples of the additives include silver nitrate (PTL 4), copper sulfate (PTL 7), and cysteine (NPL 14).

The term "culture" in this step refers to that a plant tissue is placed onto a solidified coculture medium or in a liquid coculture medium and is grown at an appropriate temperature, light-dark condition, and term. In the present invention, the embodiment of medium is not particularly limited, so far as the medium can sufficiently supply medium components to a plant tissue. The coculture medium can be solidified with a solidifying agent known in the art. A typical example of the solidifying agent is agarose. The solidified coculture medium is suitable for use in the present invention. The culture temperature in this step can be appropriately selected and is preferably 20° C. to 35° C., more preferably 23° C. The culture in this step is preferably performed in a dark place, although not limited thereto. The culture time in this step can be also appropriately selected and is preferably one to five days, more preferably two days.

(2) The Step of Physically and/or Chemically Damaging One or More Portions Selected from Radicle, Germ, and Embryonic Axis Simultaneous with and/or subsequent to the coculture step, the step of physically and/or chemically damaging one or more portions selected from a radicle, a germ, and an embryonic axis in the tissue can be performed. One feature of the present invention is enhancement of the efficiencies of gene introduction and transformation of a plant by this step.

In the present invention, nonlimiting examples of the method for "physically and/or chemically damaging one or more portions selected from a radicle, a germ, and an embryonic axis" is not particularly limited and include various physical treatments and chemical treatments. Examples of the physical treatment include, but not limited to, excision or wounding with an edged knife (for example, a scalpel) and excision or wounding with a tool (for example, tweezers) having a sharp tip. Examples of the chemical treatment include, but not limited to, treatment with an acid or alkali substance that causes a loss or reduction in function of plant cells or with an agent such as an herbicide component having cytotoxicity. In the present invention, physical "excision" of one or more portions selected from a radicle, a germ, and an embryonic axis is a preferred embodiment.

The embryo is a portion that will become a plant body and includes a radicle, a germ, and an embryonic axis. The embryonic axis is a cylindrical portion that will become the axis of an embryo, and the germ and the radicle occur from the upper end and the lower end, respectively, of the embryonic axis. Throughout the specification, the radicle, germ, and embryonic axis should have the same meanings as those usually used in the art.

Throughout the specification, the term "one or more portions selected from a radicle, a germ, and an embryonic axis" (hereinafter, referred to as "the above-mentioned portion") refers to every combination of one, two, or three portions selected from the radicle, the germ, and the embryonic axis. Specific combinations are: 1) radicle, 2) germ, 3) embryonic axis, 4) radicle and germ, 5) radicle and embryonic axis, 6) germ and embryonic axis, and 7) radicle, germ, and embryonic axis.

In the case of a *Triticum* plant that is a target of the present invention, the bud and the root do not extend in the coculture step, compared to the case of rice. Accordingly, in the present invention, when the process of excising the embryonic axis is conducted after the coculture, practically, the radicle and the germ are excised together with the embryonic axis in many cases. If the radicle and the germ are maintained to be intact when the embryonic axis is excised, the remaining radicle and germ may extend. Gene introduction mediated by *Agrobacterium* needs callus formation by dedifferentiation of the plant tissue; hence the extension of the radicle and the germ is unfavorable. Accordingly, the excision of the radicle and germ together with the embryonic axis is a preferred embodiment of the present invention. However, the object of the present invention can be achieved by excising only the embryonic axis in the state where the radicle and the germ have not sprouted yet. The most distinctive feature of the present invention is that the above-mentioned portion is physically and/or chemically damaged simultaneous with and/or subsequent to the coculture step.

Throughout the specification, the term "subsequent to the coculture step" refers to that the above-mentioned portion of a *Triticum* plant cultured in the presence of *Agrobacterium* is physically and/or chemically damaged in the resting step that is performed after the coculture step.

Throughout the specification, the term "simultaneous with the coculture step" refers to that the above-mentioned portion is physically and/or chemically damaged during the coculture step. Such a case is included in the present invention as an embodiment.

Throughout the specification, the term "simultaneous with and/or subsequent to the coculture step" refers to 1) an embodiment where the above-mentioned portion is damaged during the coculture step, for example, an embodiment where a plant tissue is taken out from a coculture medium, subjected to damaging treatment, and returned to the coculture medium, during the coculture step;

2) an embodiment where the above-mentioned portion is damaged after the coculture step and before the resting step;

3) an embodiment where the above-mentioned portion is damaged during the resting step, for example, an embodiment where a plant tissue is taken out from a resting medium, subjected to damaging treatment, and returned to the resting medium, during the resting step; and 4) an embodiment where the above-mentioned portion is damaged in a plurality of steps of any of 1) to 3) mentioned above. These embodiments are all included in the present invention.

Although the timing of the damaging is not limited, it is preferable to perform damaging within seven days from the beginning of the coculture, more preferably within one to three days from the beginning of the coculture step. Examples 2 and 3 show excision of the radicle, the germ, and the embryonic axis within one to three days from the beginning of the coculture step leads to increases in the callus induction ratio and the efficiency of gene introduction regardless of whether the plant tissue that is placed onto the coculture medium until the excision or it is transferred to the resting medium before the excision.

(3) The Resting Step

The method of producing a transformed plant of the present invention further involves a resting step and a regeneration step after the coculture step.

In the resting step, the plant tissue is cultured in a resting medium after the coculture step. In this step, *Agrobacterium* is removed from the plant cells after the coculture step, and also the plant cells are propagated.

The medium used in this step is referred to as "resting medium" throughout the specification. The resting medium may be any medium that is used for plant cell culture, and examples thereof include medium based on LS inorganic salts (NPL 27) or N6 inorganic salts (NPL 28). The resting medium in this step preferably contains an antibiotic. The antibiotic contained in the resting medium differs from that used in the selection step described below and is used for eliminating *Agrobacterium*. Cefotaxime and/or carbenicillin is, but not limited to, preferably used as the antibiotic.

The resting medium used in this step preferably contains a plant growth regulator. The plant growth regulator is preferably picloram and/or 2,4-D belonging to auxins. Since the auxins generally can dedifferentiate plant tissues, almost all plant tissues are partially or completely changed to dedifferentiated tissues (callus) in this step and the subsequent selection step. Throughout the specification, the terms "dedifferentiated tissue" and "callus" refer to a tissue that is obtained by cultivation of a part (explant) of the differentiated plant tissue in a medium containing a plant growth regulator such as an auxin or a cytokinin and is amorphous and undifferentiated cell aggregation not having the shape of the original plant tissue. Accordingly, all embodiments relating to dedifferentiated tissues, for example, the case of subjecting a dedifferentiated tissue to the resting step and the case of partially or completely dedifferentiating a differentiated plant tissue in the resting step or in the subsequent selection step are within the scope of the present invention.

The term "culture" in this step refers to that a plant tissue is placed onto a solidified resting medium or in liquid resting medium and is grown at appropriate temperature, light-dark condition, and term. In the present invention, the embodiment of medium is not particularly limited, so far as the medium can sufficiently supply medium components to a plant tissue. The resting medium can be solidified with a solidifying agent known in the art. A typical example of the solidifying agent is agarose. The culture temperature in this step can be appropriately selected and is preferably 20° C. to 35° C., more preferably 25° C. The culture in this step is preferably performed in a dark place, although not limited thereto. The culture time in this step can be also appropriately selected and is preferably one to ten days, more preferably five days.

(4) Selection Step

The selection step and the regeneration step described below are generally involved in transformation of a plant by *Agrobacterium*. The selection step is not indispensable in the method of producing the transformed plant of the present invention. For example, a desired transformant can be obtained without the selection step after a treatment for enhancement of transformation as described below. The following description on the selection step is merely exemplification, and the present invention is not limited to the following description.

In this step, a transformant is selected from the tissue obtained in the above-described steps based on whether a gene is introduced or not. The medium that is used in this step is referred to as "selection medium" throughout the specification. Examples of a usable medium as the selection medium include medium based on LS inorganic salts (NPL 27) or N6 inorganic salts (NPL 28), and, specifically, an LSD1.5 medium.

In a typical method of transformation using *Agrobacterium*, the selection medium contains an auxin, preferably 2,4-D and/or picloram. Similarly, the selection medium of the present invention preferably contains a plant growth regulator. The auxin used in this selection step is not particularly limited and is preferably 2,4-D and/or picloram. Furthermore, the selection medium may contain various optional additives.

The transformed plant can be selected by, for example, cultivation of the plant after the coculture step and/or the resting step in the selection medium containing an appropriate selective drug and selecting one having resistance to the selective drug. Any selective drug that is usually used in the art can be used in this step. For example, an antibiotic or an herbicide can be used as the selective drug. Examples of the antibiotic include hygromycin, kanamycin, and blasticidin S, and examples of the herbicide include phosphinothricin, bialaphos, and glyphosate.

In order to perform the selection step, DNA inserted into T-DNA of *Agrobacterium* needs to include not only the gene to be expressed by the plant but also, for example, a resistance gene against the selective drug. The resistance gene against the selective drug is known in the art. In this step, for example, if the selection is performed with a selection medium containing hygromycin, a gene to be expressed by a plant and a hygromycin resistance gene must be introduced in the plant.

Alternatively, a transformed plant can be selected on the basis of the sugar requirement of plant cells. Sugars assimilable by plant cells include sucrose and glucose, but it is known that plant cells cannot assimilate mannose. If a plant tissue is cultured in a medium containing only mannose as a carbon source, the plant tissue dies due to a lack of assimilable sugar. Selection based on sugar requirement utilizes this principle. That is, in order to perform this selection process, DNA inserted into T-DNA of *Agrobacterium* must include not only a gene to be expressed by a plant but also a phosphomannose isomerase (PMI) gene. In this case, plant cells containing an introduced PMI gene acquire the ability to assimilate mannose as a carbon source. As a result, only a plant tissue transformed with *Agrobacterium* as described above can grow in a medium containing mannose alone as a carbon source, whereby only the transformed plant tissue can be selected (NPL 8). Such a method is also applicable to other sugars. For example, plant cells containing an introduced xylose isomerase gene can utilize xylose as a carbon source and can be therefore applied to such a method.

Alternatively, an easily detectable gene may be introduced as a screening indicator to select a transformed plant on the basis of the expression of this gene. Examples of such a gene serving as a screening indicator include a GFP gene. Methods for detecting cells or tissues expressing such as a gene are known in the art.

This step may be repeated multiple times with medium having different composites. For example, repeating the selection step multiple times increases the concentration of the selective drug at every selection step and thus enhances the reliability of selection by the drug and the possibility of obtaining a transformed plant body. The selection step is preferably performed at least once, more preferably twice. In the case of multiple selection steps, a transformed tissue can be efficiently produced by excising the propagating portion from the tissue cultured in the medium containing the selective drug and subjecting only the propagating portion to the subsequent selection step.

The term "culture" in this step refers to that a plant tissue is placed onto a solidified selection medium or in liquid selection medium and is grown at appropriate temperature, light-dark condition, and term. In the present invention, the embodiment of medium is not particularly limited, so far as the medium can sufficiently supply medium components to a plant tissue. The selection medium can be solidified with, for example, agarose, as described above. The culture temperature in this step can be appropriately selected and is preferably 20° C. to 35° C., more preferably 25° C. The culture in this step is preferably performed in a dark place, although not limited thereto. The culture period in this step can be also appropriately selected. For example, in the case of repeating the selection step twice, selection is performed for five weeks in total, that is, two weeks for the primary selection and three weeks for the secondary selection. In the case of multiple selection steps, the selection is performed preferably for three to eight weeks, more preferably four to six weeks, in total. In the case of multiple selection steps, the culture period, culture temperature, and light-dark condition may be changed at every selection.

(5) Regeneration Step

The tissue cultured in a resting medium is, after optional selection, regenerated in a regeneration medium. The medium used in this step is referred to as "regeneration medium" throughout the specification. The regeneration medium does not contain auxins.

Examples of the regeneration medium include medium based on LS inorganic salts or N6 inorganic salts, and, specifically, an LSZ medium.

The regeneration medium may contain a selective drug. The selective drug usable in this step is the same as that defined in the selection step. Alternatively, the selective drug used in this step may be different from that used in the selection step. In such a case, the plant must contain a resistance gene against two or more selective drugs introduced from *Agrobacterium*.

The term "regeneration" in the present invention refers to that a completely or partially dedifferentiated plant tissue acquires the properties of the original plant tissue or plant body again. If an auxin is used in the coculture step and/or selection step, the plant tissue is completely or partially dedifferentiated. Accordingly, the dedifferentiated tissue is regenerated by subjecting the tissue to this step to obtain an intact transformed plant body.

The term "culture" in this step refers to that a plant tissue is placed onto a solidified regeneration medium or in liquid redifferentiation medium and is grown at appropriate temperature, light-dark condition, and term. In the present invention, he embodiment of medium is not particularly limited, so far as the medium can sufficiently supply medium components to a plant tissue. The regeneration medium can be solidified with, for example, agarose as described above. The culture temperature in this step can be appropriately selected and is preferably 20° C. to 35° C., more preferably 25° C. The culture in this step is preferably performed in the light for 16 to 24 hr per day, but is not limited thereto. The culture period can be also appropriately selected and is preferably 7 to 21 days, more preferably 14 days.

2. Treatment for Transformation Enhancement Used in the Present Invention

The method of gene introduction and the method of producing a transformed plant of the present invention may involve treatment for transformation enhancement described below. Throughout the specification, the term "treatment for transformation enhancement" represents a treatment for achieving an enhancement in transformation efficiency. Non-limiting examples of the transformation-improving treatment include those shown below and combinations thereof. Such a treatment may be performed prior to, simultaneous with, or subsequent to inoculation with *Agrobacterium*. In the case of a treatment subsequent to the inoculation with *Agrobacterium*, the treatment may be performed either before or after the excision of the embryonic axis.

a) centrifugation (see WO2002/012520: PTL 3);
    b) addition of silver nitrate and/or copper sulfate to the coculture medium (see Zhao et al., 2001: NPL 9, Ishida et al., 2003: NPL 11, PTL 4 for $AgNO_3$; WO2005/017152: PTL 7 for $CuSO_4$);
    c) thermal treatment (see WO1998/054961: PTL 2);
    d) thermal treatment and centrifugation (see WO2002/012521: PTL 5);
    e) pressurization (see WO2005/017169: PTL 6);
    f) inoculation with *Agrobacterium* in the presence of a powder (see WO2007/069643: PTL 8); and
    g) addition of cysteine to the coculture medium (Frame et al., 2002: NPL 10).

In these treatments, centrifugation, the thermal treatment, the thermal treatment and centrifugation, pressurization, and the addition of a powder enhance the efficiency of gene introduction, and the addition of silver nitrate and/or copper sulfate increases the callus induction ratio. The addition of copper sulfate to a regeneration medium enhances regeneration efficiency.

Centrifugation can be performed by, for example, but not limited to, the method described in WO2002/012520 (PTL 3). For example, before being brought into contact with *Agrobacterium*, a plant material is treated at a centrifugal acceleration of 100 to 250000 G, preferably 500 to 200000 G, most preferably 1000 to 150000 G for 1 sec to 4 hr, more preferably 1 sec to 2 hr.

Centrifugation may be performed after the coculture step. The present inventors have found that the callus induction ratio increases by subjecting wheat to the centrifugation. The conditions for such centrifugation may be the same as those described in PTL 3. Specifically, the centrifugal acceleration is usually about 100 to 250000 G, preferably about 500 to 200000 G, more preferably about 1000 to 150000 G, and most preferably about 1100 to 110000 G. The prtiod for centrifugation is appropriately selected depending on the centrifugal acceleration and is usually 1 sec or more. The upper limit of the centrifugation period is not particularly limited, and the purpose of the treatment can be usually achieved by centrifugation for about 10 min. Accordingly, centrifugation is performed for 1 sec to 4 hr, more preferably for 1 sec to 2 hr. Even if the centrifugation time is extremely short, for example, 1 sec or less, the gene introduction efficiency can be significantly enhanced at high centrifugal acceleration. On the contrary, at low centrifugal acceleration, the gene introduction efficiency can be significantly enhanced by long-period centrifugation. Incidentally, the optimum centrifugation conditions can be readily determined through routine experiments.

As described above, centrifugation may be performed before the coculture step or may be performed after the coculture step either before or after excision of the embryonic axis. Accordingly, centrifugation of a plant material before and/or after coculture is a preferred embodiment of the present invention.

The addition of silver nitrate and/or copper sulfate to the coculture medium is described in, for example, Zhao et al. 2001 (NPL 9), Ishida et al. 2003 (NPL 11), and WO2005/017152. Silver nitrate and/or copper sulfate can be added to the coculture medium in a concentration of, for example, 1 to 50 µM, preferably 1 to 10 µM.

Thermal treatment can be performed by, for example, the method described in WO1998/054961 (PTL 2). For example, before being brought into contact with *Agrobacterium*, a plant material is treated at 33° C. to 60° C., preferably 37° C. to 52° C. for 5 sec to 24 hr, preferably 1 min to 24 hr.

Thermal treatment and centrifugation can be performed by, for example, the method described in WO2002/012521 (PTL 5). The conditions for the thermal treatment and the centrifugation may be, for example, the same as those described above.

Pressurization can be performed by, for example, the method described in WO2005/017169 (PTL 6). The pressurization is performed in a range of, but not limited to, preferably 1.7 to 10 atm, more preferably 2.4 to 8 atm.

Pressurization may be performed after the coculture step. The present inventors have found that the callus induction ratio is increased by subjecting wheat to the pressurization. The conditions for such pressurization may be the same as those described in PTL 6. Pressurization may be performed before the coculture step or may be performed after the coculture step either before or after excision of the embryonic axis. Accordingly, pressurization of a plant material before and/or after coculture is a suitable embodiment of the present invention.

Inoculation with *Agrobacterium* in the presence of a powder can be performed by, for example, the method described in WO2007/069643 (PTL 8). Specifically, for example, a plant material is inoculated with a mixture of a suspension of *Agrobacterium* and a powder, or a mixture of a plant and a powder is inoculated with *Agrobacterium*. The powder is not limited, and examples thereof include porous powders, glass wool, and activated charcoal. Porous ceramics, glass wool, and activated charcoal are preferred, and hydroxyapatite, silica gel, and glass wool are more preferred.

In the treatment of adding cysteine to a coculture medium, cysteine may be added to the coculture medium in a concentration of 10 mg/L to 1 g/L, preferably 50 to 750 mg/L, and more preferably 100 to 500 mg/L.

Those skilled in the art can perform these treatments at appropriate timing and conditions. Appropriate combination of these treatments can further enhance the transformation efficiency. Accordingly, a preferred treatment for transformation enhancement are; centrifugation, addition of $AgNO_3$ and/or $CuSO_4$ to the coculture medium, thermal treatment, thermal treatment and centrifugation, pressurization, inoculation with *Agrobacterium* in the presence of a powder, addition of cysteine to the coculture medium, or a combination thereof. As shown in Examples below, a combination of centrifugation and addition of $AgNO_3$ and/or $CuSO_4$ to the coculture medium is a preferred embodiment of the present invention.

3. Effect by the Method of the Present Invention

A *Triticum* plant can be transformed at a high efficiency through the method of gene introduction of the present invention and the method of producing a transformed plant of the present invention. Accordingly, enhancement of the transformation efficiency of a plant can be achieved.

Throughout the specification, the term "high transformation efficiency" includes concepts that a target gene is introduced into a plant cell at a high efficiency, that a callus is induced from, for example, an immature embryo at a high efficiency, and that regeneration occurs from the transformed callus at a high efficiency. Throughout the specification, the term "enhanced transformation efficiency" includes the concepts that the introduction efficiency of a target gene into a plant cell is enhanced, that the callus induction ratio from, for example, an immature embryo is increased, and that the regeneration efficiency from a transformed callus is enhanced. Example 2 described below shows that the method of gene introduction of the present invention and the method of producing a transformed plant of the present invention can achieve increases in rate of callus formation and gene introduction efficiency compared to those by conventional methods.

In addition to the above, the method of gene introduction of the present invention and the method of producing a transformed plant of the present invention can provide advantageous effects such as high repeatability of transformation efficiency of a plant, a low variation between transformation experiments, and stable acquisition of a transformed plant. These effects are included in the concepts of "high transformation efficiency" and "enhanced transformation efficiency" in a broad sense.

Whether a gene is introduced into a plant tissue or not can be identified by various known processes. For example, it is possible to confirm whether transformation is achieved or not by using a gene for transformation as a reporter gene such as a β-glucuronidase (GUS) gene, a luciferase gene, or a GFP gene and visually observing the expression site of the reporter gene by a simple known method. Alternatively, it is possible to confirm whether transformation is achieved or not by using a selection marker gene such as an antibiotic resistance gene or an herbicide resistance gene, that is, the presence of transformation can be confirmed using expression of the resistance as an indicator by cultivation of the plant cells in a medium containing an antibiotic or an herbicide or treating the plant with a solution of an antibiotic or an herbicide.

Whether a gene was introduced or not is reliably determined by, for example, confirmation of insertion of a transgene into a plant chromosome by Southern hybridization and confirmation of expression of the transgene in a progeny plant (inheritance to progeny). The Southern hybridization can be performed by a well-known method, for example, described in Molecular Cloning (NPL 26). Expression in a progeny plant can be confirmed by investigating the expression of a reporter gene such as a GUS gene or the expression of a selection marker gene such as an herbicide resistance gene. The procedure is described in NPL 4, but is not limited thereto.

The efficiency of gene introduction can be determined by a calculation method usually used by those skilled in the art. For example, it can be determined by dividing the number of plant tissues to which a gene has been introduced by the number of plant tissues inoculated with *Agrobacterium*.

The rate of callus formation may be determined by, for example, by visually evaluating callus formation in a stepwise manner and calculating the average. For example, as described in Examples below, callus formation from immature embryos may be evaluated in three grades: 1 (callus formation occurring in a half or more of scutellum), 0.5 (callus formation occurring in a part of scutellum), and 0 (no callus formation occurring) (index of callus formation in Examples described below). Alternatively, the rate of callus formation may be calculated by dividing the number of formed calluses by the number of plant tissues inoculated with *Agrobacterium*.

The efficiency of regeneration from the transformed calluses may be also determined, for example, by dividing the number of regenerated calluses by the number of plant tissues inoculated with *Agrobacterium*, as in the rate of callus formation.

EXAMPLES

The present invention will now be described with reference to examples below, which are not intended to limit the technical scope of the invention. The scope of the present invention is defined by the appended claims. Based on description in the specification, modifications, and changes will be apparent to those skilled in the art.

Example 1

Effect of Coculture Medium Composition on the Efficiency of Gene Introduction

Material and Method

Immature embryos (size: 1.5 to 2.5 mm) of bread wheat (variety: Bobwhite) on the 14th day after flowering were aseptically collected and were washed once with an Inf liquid medium (1/10 concentrations of MS inorganic salt and MS vitamin, 10 g/L of glucose, 0.5 g/L of MES, pH 5.8). Pretreatment (centrifugation at 15000 rpm for 10 min) was performed for enhancing the gene introduction efficiency. *Agrobacterium* strain EHA101 (pIG121Hm) (NPL 3) was suspended at about $1.0 \times 10^9$ cfu/mL in an Inf liquid medium containing 100 µM acetosyringone to prepare an inoculation source. The inoculation source was added to the centrifugated immature embryos, and the mixture was stirred for 30 sec, followed by leaving to stand at room temperature for 5 min. The immature embryos inoculated with *Agrobacterium* were placed onto a Co-Cul coculture medium (1/10 concentrations of MS inorganic salt and MS vitamin, 10 g/L of glucose, 0.5 g/L of MES, pH 5.8, solidifying agent: 8 g/L of agarose) containing 100

μM acetosyringone or on a Co-Cul coculture medium containing 5 μM AgNO$_3$ and 5 μM CuSO$_4$ in such a manner that the scutellum faced upward. As a control medium, a Co-Cul coculture medium containing 0.5 mg/L of 2,4-D and 2.2 mg/L of picloram was used.

The immature embryos were cultured at 23° C. in the dark for 2 days, and then radicles, germs, and embryonic axes were excised therefrom using a scalpel and tweezers. Subsequently, the embryos were placed onto a resting medium containing MS inorganic salt and MS vitamin, 40 g/L of maltose, 0.5 g/L of glutamine, 0.1 g/L of casein hydrolysate, 0.75 g/L of magnesium chloride hexahydrate, 1.95 g/L of MES, pH 5.8, 2 g/L of Gelrite as a solidifying agent, 100 mg/L of ascorbic acid, 5 μM AgNO$_3$, 250 mg/L of carbenicillin, 100 mg/L of cefotaxime, 2.2 mg/L of picloram, and 0.5 mg/L of 2,4-D, and the embryos were cultured at 25° C. in the dark for 5 days. The immature embryos were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, expression of a GUS gene was investigated.

Results

In the immature embryos cultured in control coculture medium containing 2,4-D and picloram as plant growth regulators, blue spots indicating transient expression of the GUS gene were not observed in any of 25 immature embryo after staining with X-gluc. On the other hand, in the immature embryos cultured in the coculture medium not containing the plant growth regulators, in three of eighteen immature embryos, blue spots having a diameter of 1 mm or more were observed. Furthermore, in the immature embryos cultured in the coculture medium containing silver nitrate and copper sulfate and not containing the plant growth regulators, in seven of eighteen immature embryos, blue spots having a diameter of 1 mm or more were observed.

Thus, it was revealed that the efficiency of gene introduction was enhanced by removing plant growth regulators from the coculture medium and that gene introduction was further promoted by adding silver nitrate and copper sulfate to the medium.

Example 2

Effect of Excision of Radicle, Germ, and Embryonic Axis on Callus Formation and Efficiency of Gene Introduction (Immature Embryos were Placed onto Coculture Medium Until Excision)

Material and Method

Immature embryos (size: 1.5 to 2.5 mm) of bread wheat (variety: Bobwhite) on the 14th day after flowering were aseptically collected and were washed once with an Inf liquid medium (1/10 concentrations of MS inorganic salt and MS vitamin, 10 g/L of glucose, 0.5 g/L of MES, pH 5.8). Pretreatment (centrifugation at 15000 rpm for 10 min) was performed for enhancing the efficiency of gene introduction. *Agrobacterium* strain EHA101 (pIG121Hm) (NPL 3) was suspended at about 1.0×10$^9$ cfu/mL in an Inf liquid medium containing 100 μM acetosyringone to prepare an inoculation source. The inoculation source was added to the centrifugated immature embryos, and the mixture was stirred for 30 sec, followed by leaving to stand at room temperature for 5 min. Immature embryos as a control were inoculated with *Agrobacterium* after excision of the radicles, germs, and embryonic axes using a scalpel and tweezers. Other immature embryos were inoculated with *Agrobacterium* without excising the radicles, germs, and embryonic axes. These immature embryos were placed onto a Co-Cul coculture medium (1/10 concentrations of MS inorganic salt and MS vitamin, 10 g/L of glucose, 0.5 g/L of MES, pH 5.8, solidifying agent: 8 g/L of agarose) containing 100 μM acetosyringone and 5 μM AgNO$_3$ and 5 μM CuSO$_4$ in such a manner that the scutellum faced upward and were cocultured at 23° C. in the dark.

On each of the 1st, 2nd, and 3rd days from the beginning of the coculture, the radicles, germs, and embryonic axes were excised from about 40 immature embryos using a scalpel and tweezers, and the immature embryos were placed onto a resting medium containing MS inorganic salt and MS vitamin, 40 g/L of maltose, 0.5 g/L of glutamine, 0.1 g/L of casein hydrolysate, 0.75 g/L of magnesium chloride hexahydrate, 1.95 g/L of MES, pH 5.8, 2 g/L of Gelrite as a solidifying agent, 100 mg/L of ascorbic acid, 5 μM AgNO$_3$, 250 mg/L of carbenicillin, 100 mg/L of cefotaxime, 2.2 mg/L of picloram, and 0.5 mg/L of 2,4-D. The control immature embryos from which the radicles, germs, and embryonic axes were excised before inoculation with *Agrobacterium* were placed onto a resting medium on the 2nd day from the beginning of the coculture. A part of the immature embryos were also placed onto a resting medium on the 2nd day from the beginning of the coculture without excising the radicles, germs, and embryonic axes therefrom. After cultivation at 25° C. in the dark for 7 to 9 days, the callus formation from the immature embryos was evaluated in three grades (index of callus formation): 1 (callus formation occurring in a half or more of scutellum), 0.5 (callus formation occurring in a part of scutellum), and 0 (no callus formation occurring).

A part of the immature embryos of which embryonic axes were excised on the 2nd day from the beginning of the coculture and a part of the control immature embryos of which embryhonic axes were excised before the inoculation with *Agrobacterium* were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, expression of a GUS gene was investigated.

Results

1) Callus Formation

FIG. 1 shows the results of callus formation. In FIG. 1, the vertical axis represents callus formation from immature embryos, while the horizontal axis represents days from inoculation with *Agrobacterium* to placement of immature embryos after excision of the radicles, germs, and embryonic axes onto a resting medium. The highest rate of callus formation was observed in the immature embryos from which the radicles, germs, and embryonic axes were excised on the 1st day from the beginning of the coculture and then placed onto the resting medium. The rate of callus formation lowered with an increase in the time until the radicles, germs, and embryonic axes were excised. The rate of callus formation when the immature embryos were placed onto a resting medium on the 2nd day from the beginning of the coculture after excision of the radicles, germs, and embryonic axes on the same day was higher than the case where the immature embryos were placed onto a resting medium on the 2nd day from the beginning of the coculture without excising the radicles, germs, and embryonic axes (FIG. 1: 2nd day without excision). In the immature embryos inoculated with *Agrobacterium* after excision of the radicles, germs, and embryonic axes (FIG. 1: 0th day), almost no callus formation was observed.

The index of callus formation of the immature embryos from which the radicles, germs, and embryonic axes were excised on the 1st day from the beginning of the coculture was 0.51 (FIG. 1: 1st day), whereas the index of callus formation of the immature embryos inoculated with *Agrobacterium* after excising the radicles, germs, and embryonic axes was 0.10 (FIG. 1: 0th day) and the index of callus formation of the immature embryos cultured on a resting medium without excising the radicles, germs, and embryonic axes was 0.33 (FIG. 1: 2nd day without excision). Accordingly, the rate of callus formation increased by 5 times compared to the conventional method where the radicle, germ, and embryonic axis were excised before inoculation with *Agrobacterium* and by 1.5 times compared to the conventional method where the embryonic axis was not excised.

2) Efficiency of Gene Introduction

In the immature embryos inoculated with *Agrobacterium* after excision of the radicles, germs, and embryonic axes, one of 18 immature embryos expressed the GUS gene, while in the immature embryos from which the radicles, germs, and embryonic axes were excised on the 2nd day from the beginning of the coculture, 15 of 19 immature embryos expressed the GUS gene.

Example 3

Effect of Excision of Radicle, Germ, and Embryonic Axis on Callus Formation and Efficiency of Gene Introduction (Immature Embryos were Placed onto a Resting Medium on the 2nd Day from the Beginning of the Coculture after Inoculation, Independently of the Day of the Excision)

Material and Method

Immature embryos (size: 1.5 to 2.5 mm) of bread wheat (variety: Bobwhite) on the 14th day after flowering were aseptically collected and were washed once with an Inf liquid medium (1/10 concentrations of MS inorganic salt and MS vitamin, 10 g/L of glucose, 0.5 g/L of MES, pH 5.8). Pretreatment (centrifugation at 15000 rpm for 10 min) was performed for enhancing the efficiency of gene introduction. *Agrobacterium* strain EHA101 (pIG121Hm) (NPL 3) was suspended at about $1.0\times10^9$ cfu/mL in an Inf liquid medium containing 100 μM acetosyringone to prepare an inoculation source. The inoculation source was added to the centrifugated immature embryos, and the mixture was stirred for 30 sec, followed by leaving to stand at room temperature for 5 min. The immature embryos inoculated with *Agrobacterium* were placed onto a Co-Cul coculture medium (1/10 concentrations of MS inorganic salt and MS vitamin, 10 g/L of glucose, 0.5 g/L of MES, pH 5.8, solidifying agent: 8 g/L of agarose) containing 100 μM acetosyringone, 5 μM $AgNO_3$, and 5 μM $CuSO_4$ in such a manner that the scutellum faced upward, and were cocultured at 23° C. in the dark.

On each of the 0th, 1st, 2nd, 3rd, 4th, and 5th days from the beginning of the coculture, the radicles, germs, and embryonic axes were excised from 15 or 16 immature embryos using a scalpel and tweezers. The immature embryos from which the radicles, germs, and embryonic axes were excised immediately (0th day) after the beginning of the coculture were cultured for 2 days in a Co-Cul coculture medium and were then placed onto a resting medium containing MS inorganic salt and MS vitamin, 40 g/L of maltose, 0.5 g/L of glutamine, 0.1 g/L of casein hydrolysate, 0.75 g/L of magnesium chloride hexahydrate, 1.95 g/L of MES, pH 5.8, 2 g/L of Gelrite as a solidifying agent, 100 mg/L of ascorbic acid, 5 μM $AgNO_3$, 250 mg/L of carbenicillin, 100 mg/L of cefotaxime, 2.2 mg/L of picloram, and 0.5 mg/L of 2,4-D.

In this Example, the immature embryos were placed onto a resting medium on the 2nd day from the beginning of the coculture after inoculation, independently of the day of the excision. The immature embryos from which the radicles, germs, and embryonic axes were excised on the 1st day from the beginning of the coculture were cultured in a Co-Cul coculture medium for further one day and then placed onto a resting medium. The immature embryos from which the radicles, germs, and embryonic axes were excised on the 2nd day from the beginning of the coculture were placed onto a resting medium immediately after the excision of the radicles, germs, and embryonic axes. Other immature embryos were all placed onto a resting medium on the 2nd day from the beginning of the coculture without excising the radicles, germs, and embryonic axes. In these immature embryos, the radicles, germs, and embryonic axes were excised on the 1st, 2nd, and 3rd day from the placement onto the resting medium (that is, 3rd, 4th, and 5th day from the beginning of the coculture), and the immature embryos were continuously cultured on the resting medium. A part of the immature embryos were placed onto a resting medium on the 2nd day from the beginning of the coculture and were cultured thereon without excising the radicles, germs, and embryonic axes (without excision). After cultivation at 25° C. in the dark for 7 days, the callus formation from the immature embryos was evaluated in three grades (index of callus formation): 1 (callus formation occurring in a half or more of scutellum), 0.5 (callus formation occurring in a part of scutellum), and 0 (no callus formation occurring).

The immature embryos after evaluation of callus formation were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, the number of immature embryos expressing a GUS gene was counted.

Results

1) Callus Formation

Figure 2:
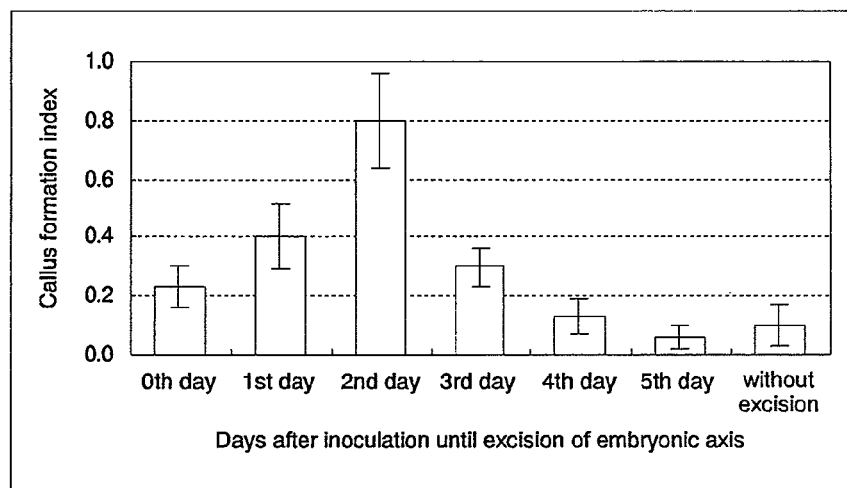
FIG. 2 is a graph showing the effect of excision of a radicle, a germ, and an embryonic axis on callus formation from wheat immature embryos inoculated with *Agrobacterium*. In the experiments shown in FIG. 2, the wheat immature embryos were placed onto a resting medium on the 2nd day from the beginning of the coculture after inoculation, independently of the day of the excision. The vertical axis represents the index of callus formation from immature embryos, and the horizontal axis represents days from inoculation with *Agrobacterium* until excision of radicles, germs, and embryonic axes from the immature embryos. The callus formation indices are determined as in those in FIG. 1. The "0th day" on the horizontal axis represents immature embryos from which the embryonic axes were excised before inoculation with *Agrobacterium*. The "without excision" represents immature embryos placed onto a resting medium on the 2nd day from the inoculation with *Agrobacterium* without excision of the embryonic axes.

FIG. 2 shows the results of callus formation. In FIG. 2, the vertical axis represents the index of callus formation from immature embryos, while the horizontal axis represents days from inoculation with *Agrobacterium* to excision of the radicles, germs, and embryonic axes. The highest index of callus formation was observed in the immature embryos from which the radicles, germs, and embryonic axes were excised on the 2nd day from the beginning of the coculture and then placed onto the resting medium. The rate of callus formation lowered with an increase in the time until the radicles, germs, and embryonic axes were excised. The index of callus formation of the immature embryos that were placed onto a resting medium on the 2nd day from the beginning of the coculture without excising the radicles, germs, and embryonic axes (without excision) was equivalent to that of the immature embryos from which the radicles, germs, and embryonic axes were excised on the 5th day from the beginning of the coculture. The index of callus formation of the immature embryos that were inoculated with *Agrobacterium* after excision of the radicles, germs, and embryonic axes was equivalent to that of the immature embryos from which the radicles, germs, and embryonic axes were excised immediately after the beginning of coculture (0th day).

The index of callus formation of the immature embryos that were inoculated with *Agrobacterium* after excision of the radicles, germs, and embryonic axes and the index of callus formation of the immature embryos from which the radicles, germs, and embryonic axes were excised immediately after the beginning of the coculture were 0.23 (FIG. 2: 0th day), whereas the index of callus formation of the immature embryos that were subjected to resting culture without excising the radicles, germs, and embryonic axes was 0.10 (FIG. 2: without excision). The index of callus formation of the immature embryos from which the radicles, germs, and embryonic axes were excised on the 1st day from the beginning of the coculture was 0.40 (FIG. 2: 1st day). The index of callus formation of the immature embryos from which the radicles, germs, and embryonic axes were excised on the 2nd day from the beginning of the coculture was 0.80 (FIG. 2: 2nd day). The index of callus formation of the immature embryos from which the radicles, germs, and embryonic axes were excised on the 3rd day from the beginning of the coculture was 0.30 (FIG. 2: 3rd day). The index of callus formation of the immature embryos from which the radicles, germs, and embryonic axes were excised on the 4th day from the beginning of the coculture was 0.13 (FIG. 2: 4th day). The index of callus formation of the immature embryos from which the radicles, germs, and embryonic axes were excised on the 5th day from the beginning of the coculture was 0.06 (FIG. 2: 5th day). Accordingly, comparison of data (FIG. 2: 2nd day) of immature embryos from which the radicles, germs, and embryonic axes were excised on the 2nd day revealed that the rate of callus formation increased by 3.5 times that in the conventional method where the radicle, germ, and embryonic axis were excised before inoculation with *Agrobacterium* (FIG. 2: 0th day) and by 8 times that in the conventional method where the embryonic axis was not excised (FIG. 2: without excision).

2) Efficiency of Gene Introduction

In the immature embryos inoculated with *Agrobacterium* after excision of the radicles, germs, and embryonic axes, one of 15 immature embryos expressed the GUS gene, while in the immature embryos from which the radicles, germs, and embryonic axes were excised on the 2nd day from the beginning of the coculture, 8 of 15 immature embryos expressed the GUS gene. In the immature embryos from which the radicles, germs, and embryonic axes were excised on the 3rd day from the beginning of the coculture, 11 of 15 immature embryos expressed the GUS gene. In the immature embryos from which the radicles, germs, and embryonic axes were excised on the 4th day from the beginning of the coculture, 9 of 15 immature embryos expressed the GUS gene. In the immature embryos from which the radicles, germs, and embryonic axes were excised on the 5th day from the beginning of the coculture, 7 of 16 immature embryos expressed the GUS gene. In the immature embryos cultured in a resting medium without excising the radicles, germs, and embryonic axes, only 3 immature embryos of 15 immature embryos expressed the GUS gene.

Example 4

Production of Transformed Plant

Material and Method

Bread wheat (variety: Bobwhite) was cultivated in an artificial weather room KG-206SHL (Koito Kogyo K.K.), a greenhouse equipped with an air conditioner, or an ordinary glass house, and the immature embryos (size: 1.5 to 2.5 mm) of the bread wheat were aseptically collected on the 14th day after flowering and were washed once with an Inf liquid medium (1/10 concentrations of MS inorganic salt and MS vitamin, 10 g/L of glucose, 0.5 g/L of MES, pH 5.8). Pretreatment (centrifugation at 15000 rpm for 10 min) was performed for enhancing the efficiency of gene introduction. *Agrobacterium* strain EHA101 (pIG121Hm) (NPL 3) was suspended at about $1.0 \times 10^9$ cfu/mL in an Inf liquid medium containing 100 µM acetosyringone to prepare an inoculation source. The inoculation source was added to the centrifugated immature embryos, and the mixture was stirred for 30 sec, followed by leaving to stand at room temperature for 5 min. The immature embryos inoculated with *Agrobacterium* were placed onto a Co-Cul coculture medium (1/10 concentrations of MS inorganic salt and MS vitamin, 10 g/L of glucose, 0.5 g/L of MES, pH 5.8, solidifying agent: 8 g/L of agarose) containing 100 µM acetosyringone, 5 nM $AgNO_3$, and 5 µM $CuSO_4$ in such a manner that the scutellum faced upward, and were cocultured at 23° C. in the dark.

On the 2nd day from the beginning of the coculture, the radicles, germs, and embryonic axes were excised from the immature embryos using a scalpel and tweezers. The immature embryos were placed onto a resting medium containing MS inorganic salt and MS vitamin, 40 g/L of maltose, 0.5 g/L of glutamine, 0.1 g/L of casein hydrolysate, 0.75 g/L of magnesium chloride hexahydrate, 1.95 g/L of MES, pH 5.8, 2 g/L of Gelrite as a solidifying agent, 100 mg/L of ascorbic acid, 5 µM $AgNO_3$, 250 mg/L of carbenicillin, 100 mg/L of cefotaxime, 2.2 mg/L of picloram, and 0.5 mg/L of 2,4-D, followed by cultivation at 25° C. in the dark for 5 days. Subsequently, the immature embryos were placed onto a primary selection medium that is a resting medium containing 15 mg/L of hygromycin, followed by cultivation under the same conditions for 2 weeks. Subsequently, the immature embryos were placed onto a secondary selection medium that is a resting medium containing 30 mg/L of hygromycin.

The immature embryos were cultured under the same conditions for 3 weeks and then were placed onto an LSZ medium (NPL 4) containing 30 mg/L of hygromycin, followed by cultivation at 25° C. in the light for 2 weeks. The regenerated plants were placed onto an LSF medium (NPL 16) containing 15 mg/L of hygromycin and were cultured under the same conditions for 2 weeks. The plants having rooting were placed onto an LSF medium not containing hygromycin and were cultivated for 1 to 2 weeks. The plants having sufficient rooting were transplanted to a pot containing soil and were cultivated in an artificial weather machine. A part of leaves of the regenerated plants were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, expression of a GUS gene was investigated.

Results

Tests were performed seven times in total during from April to May in 2008 and from December in 2008 to March in 2009. The results are shown in Table 1. The wheat as a raw material was collected from those cultivated in an artificial weather room (artificial weather machine), a greenhouse equipped with an air conditioner (air conditioning greenhouse), and an ordinary glass house (ordinary greenhouse). In Table 1, transformation efficiency represented by (B)/(A) is shown in the rightmost column, wherein (A) represents the number of inoculated immature embryos and (B) represents the number of plant individuals that are hygromycin resistance and GUS positive.

In each test, one or two individual regenerated plants showing hygromycin resistance were obtained from the inoculated immature embryos. All of the obtained plants expressed the GUS gene to show that the gene was introduced to provide transformed plants. These transformed plants all had normal shapes and fertility. In conclusion, it is apparent that the method of the present invention can stably provide transformed wheat even if plants cultivated at different times under different environments are used as raw materials.

TABLE 1

Results of wheat transformation

| Test No. | Date of inoculation | Cultivation of material | Number of inoculated immature embryos (A) | Number of HmR, GUS+ plants (B) | Transformation efficiency B/A (%) |
|---|---|---|---|---|---|
| 1 | Apr. 22, 2008 | Ordinary greenhouse | 17 | 1 | 5.9 |
| 2 | May 23, 2008 | Artificial weather machine | 17 | 1 | 5.9 |
| 3 | Dec. 9, 2008 | Air conditioning greenhouse | 39 | 2 | 5.1 |
| 4 | Dec. 10, 2008 | Air conditioning greenhouse | 32 | 2 | 6.3 |
| 5 | Jan. 15, 2009 | Air conditioning greenhouse | 20 | 1 | 5.0 |
| 6 | Feb. 12, 2009 | Air conditioning greenhouse | 20 | 1 | 5.0 |
| 7 | Mar. 3, 2009 | Air conditioning greenhouse | 21 | 2 | 9.5 |

HmR: Hygromycin resistance,
GUS+: GUS positive

Example 5

Southern Analysis

Material and Method

DNA was extracted in accordance with the method of Komari et al. (NPL 29) from leaves of the transformed plant expressing the GUS gene obtained in Example 3. The extracted DNA was treated with restriction enzyme HindIII, and the transgene was detected by a Southern method using the GUS gene as a probe. The Southern method was performed in accordance with the method described in Molecular Cloning (NPL 26).

Results

Every transformant showed a band that hybridized with the GUS probe. The patterns of the respective transformants differ from one another to show that the transgene was randomly inserted on the chromosomes of the plants. The number of bands of each GUS positive individual was one to three to reveal that the copy number of the inserted transgene was small in every transformant. Table 2 shows the number of individuals of each T0 plant to which the GUS gene was introduced at a copy number of 1 to 3.

TABLE 2

The number of copies of the GUS gene in transformed generation plant (T0)

| | The number of copies of the GUS gene | | |
|---|---|---|---|
| | 1 | 2 | 3 |
| The number of plant individuals | 3 | 3 | 1 |

Example 6

Inheritance of Transgene to Progeny

Material and Method

T1 seeds were obtained by cultivating the transformed plant obtained in Example 3. The T1 seeds were seeded in potting soil and were cultivated in a greenhouse. Leaves were cut from seedling on the 11th day from the seeding and were put into an ELA medium (NPL 16) containing 200 mg/L of hygromycin. After cultivation at 25° C. in the light for 6 days, each leaf piece was investigated to determine whether it is green (hygromycin resistant) or yellow (hygromycin sensitive).

Results

In every progeny plant of the investigated four lines, segregation of hygromycin-resistant and sensitive was observed. The segregation ratio was 3:1 in all cases to confirm that the transgene was inherited to the progeny plants according to Mendel's laws (Table 3).

TABLE 3

Inheritance of transgene to progeny

| | Number of T1 plants | | | |
|---|---|---|---|---|
| Line (T0) | Hygromycin resistant | Hygromycin sensitive | Resistant:Sensitive | $\chi^2$ |
| 001 | 16 | 4 | 3:1 | 0.27 |
| 011 | 25 | 5 | 3:1 | 1.11 |
| 015 | 19 | 6 | 3:1 | 0.01 |
| 019 | 37 | 13 | 3:1 | 0.03 |

Reference Example

Followup Experiment of Wheat Transformation by Conventional Method

Material and Method

1) Common method of Wan and Layton (2006)

In accordance with a common method of Wan and Layton (2006) (NPL 23), bread wheat (variety: Bobwhite) was used as a raw material, and the immature embryos immediately after harvesting and the immature embryos cultured in a CM4C medium (MS inorganic salt and MS vitamin, 0.5 g/L of glutamine, 0.1 g/L of casein hydrolysate, 0.75 g/L of magnesium chloride hexahydrate, 40 g/L of maltose, 0.5 mg/L of 2,4-D, 2.2 mg/L of picloram, 1.95 g/L of MES, pH 5.8, 2 g/L of Gelrite as a solidifying agent, and 100 mg/L of ascorbic acid) for two days (pre-cultured immature embryos) were inoculated with EHA101 (pIG121Hm) suspended in a CM4C liquid medium in which the concentrations of MS inorganic salt and MS vitamin were reduced to $\frac{1}{10}$. The immature embryos and the pre-cultured immature embryos after inoculation were placed onto a coculture medium in which the concentrations of MS inorganic salt and MS vitamin were reduced to 1/10 and containing 10 g/L of glucose and 200 μM acetosyringone.

The immature embryos and the pre-cultured immature embryos after the coculture were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, expression of a GUS gene was investigated.

Regarding the method of Wan and Layton (2006), the introduction of the publication which cites the literature mentions that the protocols described in the publication are the most effective experimental approaches provided by leaders and veterans in each field (NPL 32).

Results

Table 4 shows the results of gene introduction by the method of Wan and Layton (2006). In Table 4, GUS++ represents that the immature embryos showed multiple blue spots, and GUS+ represents that the immature embryos showed one blue spot. In the immature embryos and the pre-cultured immature embryos inoculated by the method of Wan and Layton (2006), no blue spot showing transient expression of the GUS gene was observed in all tissues tested.

Thus, in the follow up experiment by the common method, the gene was not introduced into the tested materials.

TABLE 4

Followup experiment of method of Wan and Layton (2006)

| Inoculation method | Inoculation material | Number of inoculations | GUS expression ++ | + |
|---|---|---|---|---|
| Wan and Layton (2006) | Immature embryo | 19 | 0 | 0 |
| | Precultured immature embryo | 19 | 0 | 0 |

GUS++: multiple blue spots for a single immature embryo
GUS+: a single blue spot for a single immature embryo Example 7

Effect of the Time of Centrifugation on Production of Transformed Plant

Material and Method

An Icat-GUS-Tnos fragment was obtained by PCR using pIG121Hm as a template and a primer set of BglII-Icat_Fw (5'-ACT CTA GAA CAT AGA TCT CTA CAG GGT AAA TTT CTA G-3': SEQ ID NO: 1) and BamHI-GNos_Rv (5'-TTT GGA TCC GCG TCG ACG CGT CGA CGC GTC CTA GAA GCT AAT T-3': SEQ ID NO: 2). This PCR product was purified by electrophoresis, cutting, and a β-agarase treatment and was cloned into a pUC19/SmaI vector to obtain "pUC-IcatGusTnos". This pUC-IcatGusTnos was digested with BamHI+BglI+BglII, and IcatGusTnos/BamHI+BglII fragments were collected and were cloned into a pIG121Hm/BamHI+BAP vector. The resulting constructs were sequenced, and a construct having deletion of P35S—HPT was defined as "pIG121del".

Fragment A was obtained by PCR using pSB200 as a template and a primer set of BamHI-Pubi_Fw (5'-ACT CTA GAA CAT AGA TCT CTA CAG GGT AAA TTT CTA G-3': SEQ ID NO: 3) and Bar-Iubi_Rv (5'-TCG TTC TGG GTC CAT ATC TCA TTG CCC CCC GGG ATG CTC TAG AGT C-3': SEQ ID NO: 4). Then, Fragment B was obtained by PCR using pCR-35SBAR as a template and a primer set of Iubi-Bar_Fw (5'-GGG GGG CAA TGA GAT ATG GAC CCA GAA CGA CGC CCG GCC GAC ATC-3': SEQ ID NO: 5) and pIG121-BarRv (5'-CTT TGG ATC CCG GTC GGC TAC TAC TCT CAG ATC TCG GTG ACG GG-3': SEQ ID NO: 6). Fragments A and B were purified by electrophoresis, cutting, and a β-agarase treatment, and a Pubi-Iubi-BAR fragment was obtained by PCR using a mixture of Fragments A and B as a template and a primer set of BamHI-Pubi_Fw and pIG121-Bar_Rv. This PCR product was purified by electrophoresis, cutting, and a β-agarase treatment and was cloned by Zero Blunt TOPO PCR Cloning Kit for Sequencing (Invitrogen) to obtain "pCR4—PubilubiBAR". This pCR4—PubilubiBAR was digested with BamHI-HF, and the resulting fragments were purified by electrophoresis, cutting, and a β-agarase treatment and were ligated into "pIG121-PubiIubiBAR". The pIG121-PubiIubiBAR was introduced into EHA105 (Hood et al., (1993), Transgenic Research, 2: 208-218) to obtain HA105 (pIG121-PubiIubiBAR).

Bread wheat (variety: Fielder) was cultivated in a greenhouse equipped with an air conditioner, and the immature embryos (size: 1.5 to 3.0 mm) of the bread wheat were aseptically collected on the 14th day after flowering and were washed once with an Inf liquid medium. The immature embryos were divided into three groups A, B, and C each including about 50 immature embryos and were subjected to the following inoculation, coculture, and excision of embryonic axes. The immature embryos in the group A were washed once with an Inf liquid medium and were then pretreated (centrifugation at 15000 rpm for 10 min) in the Inf liquid medium to enhance the efficiency of gene introduction. The immature embryos in the groups B and C were left in the same liquid medium as above at room temperature for 10 min. Agrobacterium strain EHA101 (pIG121Hm) was suspended at about $1.0 \times 10^9$ cfu/mL in an Inf liquid medium containing 100 μM acetosyringone to prepare an inoculation source. The inoculation source was added to the immature embryos of each of the groups A, B, and C, and the mixture was stirred for 30 sec, followed by leaving to stand at room temperature for 5 min. The immature embryos inoculated with Agrobacterium were placed onto a Co-Cul coculture medium containing 100 μM acetosyringone, 5 μM AgNO$_3$, and 5 μM CuSO$_4$ in such a manner that the scutellum faced upward, and were cocultured at 23° C. in the dark.

On the 2nd day from the beginning of the coculture, the radicles, germs, and embryonic axes were excised from the immature embryos in the group A using a scalpel and tweezers. The immature embryos were placed onto a resting medium (the composition was the same as that described in Example 1). Similarly, the radicles, germs, and embryonic axes were excised from the immature embryos in the group B using a scalpel and tweezers, and the immature embryos were centrifuged in an LS-inf liquid medium at 15000 rpm for 10 min and were then placed onto a resting medium. The immature embryos in the group C were centrifuged in an LS-inf liquid medium at 15000 rpm for 10 min, and the radicles, germs, and embryonic axes were excised using a scalpel and tweezers, and the immature embryos were placed onto a resting medium. The immature embryos in all the groups A, B, and C were cultured at 25° C. in the dark for 5 days. Subsequently, a part of the immature embryos were collected and immersed in a 0.1 M phosphate buffer (pH 6.8) containing 0.1% Triton X-100 at 37° C. for 1 hr.

The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, the immature embryos in each group were evaluated for expression of the GUS gene in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression). The residual immature embryos were placed onto a primary selection medium that was a resting medium containing 5 mg/L of phosphinothricin (PPT), followed by cultivation under the same conditions above for 2 weeks. Subsequently, the immature embryos were placed onto a secondary selection medium that was a resting medium containing 10 mg/L of PPT.

The immature embryos were cultured under the same conditions for 3 weeks, and were placed onto an LSZ medium containing 5 mg/L of PPT, followed by cultivation at 25° C. in the light for 2 weeks. Regenerated plants were placed onto an LSF medium containing 5 mg/L of PPT, followed by cultivation under the same conditions for 2 weeks. A regenerated individual having rooting was defined as a transformant, and the number thereof was investigated.

Results

Figure 3:
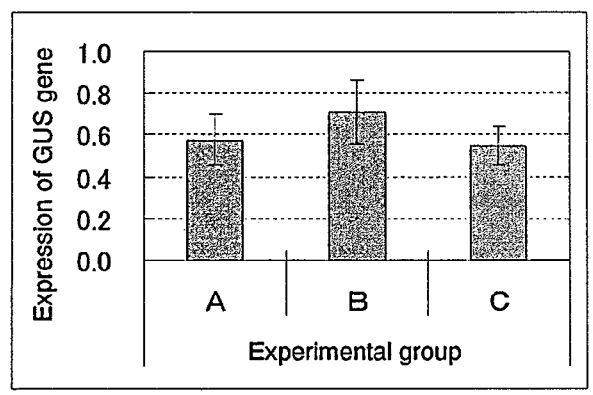
FIG. 3 is a graph showing the results of evaluation of the effect of the timing of centrifugation on the transformation efficiency.

A part of the immature embryos in each test group was harvested on the 5th day of the resting culture, and the GUS gene was expressed. The results are shown in FIG. 3. The vertical axis in FIG. 3 represents efficiencies of gene introduction evaluated by expression of the GUS gene. In every group, a half or more of the tested immature embryos expressed the GUS gene and the degrees of gene introduction were the same. Thus, it was shown that in the method of the present invention, centrifugation may be performed before the inoculation with *Agrobacterium* or may be performed after coculture and that in the case of performing the centrifugation after coculture, the centrifugation may be performed before the excision of embryonic axes or after the excision.

Table 5 shows transformation efficiencies in the immature embryos in each group. In Table 5, each transformation efficiency (E)/(D) is shown in the rightmost column, wherein (D) represents the number of inoculated immature embryos and (E) represents the number of plant individuals showing phosphinothricin (PPT) resistance.

In each test, individual regenerated plants showing PPT resistance were obtained at a high efficiency of 20% or more from the inoculated immature embryos. These transformed plants all had normal shapes. Thus, it is revealed that the method of the present invention can stably provide transformed wheat at a high efficiency regardless of the timing of centrifugation (before or after coculture or before or after excision of embryonic axis).

Example 8

Southern Analysis in Progeny Plant

Material and Method

DNA was extracted in accordance with the method of Komari et al. from leaves of transformed plants of independent three lines being positive in expression of the GUS gene obtained in Example 3 and from leaves of transformed plants of T1 generation grown from progeny seeds obtained by inbreeding the transformed plants above and being positive or negative in expression of the GUS gene. The extracted DNA was treated with restriction enzyme HindIII, and the transgene was detected by a Southern method using the GUS gene as a probe. The Southern method was performed in accordance with the method described in Molecular Cloning.

Results

The transformants being positive in expression of the GUS gene in the transformed generation and T1 generation both showed bands that hybridize with a GUS probe. The patterns of the respective transformation lines differ from one another; however, the number and the size of the bands shown by the transformed generation plant and the T1 plant were the same in every line. In the T1 generation plant being negative in expression of the GUS gene, bands that hybridize with the GUS probe were not observed in every line. Thus, it was molecularly confirmed that a transgene was stably inherited to progeny plants.

Example 9

Effect of Addition of Plant Hormone to Coculture Medium on Production of Transformed Plant Material and Method Bread wheat (variety: Fielder) was cultivated in a greenhouse equipped with an air conditioner, and the immature embryos (size: 1.5 to 3.0 mm) of the bread wheat were aseptically collected on the 14th day after flowering and were washed once with an Inf liquid medium. Pretreatment (centrifugation at 15000 rpm for 10 min) was performed to enhance the efficiency of gene introduction in an Inf liquid medium. *Agrobacterium* strain EHA101 (pIG121Hm) was suspended at about $1.0 \times 10^9$ cfu/mL in an Inf liquid medium containing 100 μM acetosyringone to prepare an inoculation source. The inoculation source was added to the immature embryos, and the mixture was stirred for 30 sec, followed by leaving to stand at room temperature for 5 min. The immature embryos inoculated with *Agrobacterium* were placed onto a Co-Cul coculture medium containing 100 μM acetosyrin-

TABLE 5

Results of transformation in immature embryos centrifugated at different timings

| Test group | Treatment timing | | Number of immature embryos | | Transformation efficiency (E/D, %) |
|---|---|---|---|---|---|
| | Centrifugation | Excision of embryonic axis | Inoculation (D) | Production of PPT resistant plant (E) | |
| A | Before inoculation | After centrifugation | 25 | 9 | 36.0 |
| B | After inoculation | Before centrifugation | 21 | 5 | 23.8 |
| C | After inoculation | After centrifugation | 21 | 7 | 33.3 | gone, 5 µM AgNO₃, and 5 µM CuSO₄ and also containing 5 µM kinetin or 4PU; 0.5 µM 2,4-D, dicamba, or picloram; or 5 µM 2,4-D, dicamba, or picloram in such a manner that the scutellum faced upward, and were cocultured at 23° C. in the dark. As a control, a Co-Cul coculture medium not containing any plant hormone was used.

On the 2nd day from the beginning of the coculture, the radicles, germs, and embryonic axes were excised using a scalpel and tweezers. The immature embryos were placed onto a resting medium (the composition is the same as that described in Example 1), followed by cultivation at 25° C. in the dark for 5 days. Subsequently, 10 to 19 immature embryos were collected from each group and were immersed in a 0.1 M phosphate buffer (pH 6.8) containing 0.1% Triton X-100 at 37° C. for 1 hr. The phosphate buffer was removed, and a phosphate buffer containing 1.0 mM 5-bromo-4-chloro-3-indolyl-β-D-glucuronic acid (X-gluc) and 20% methanol was added thereto. After treatment at 37° C. for 24 hr, the immature embryos in each group were evaluated for expression of the GUS gene in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression).

Results

Figure 4:
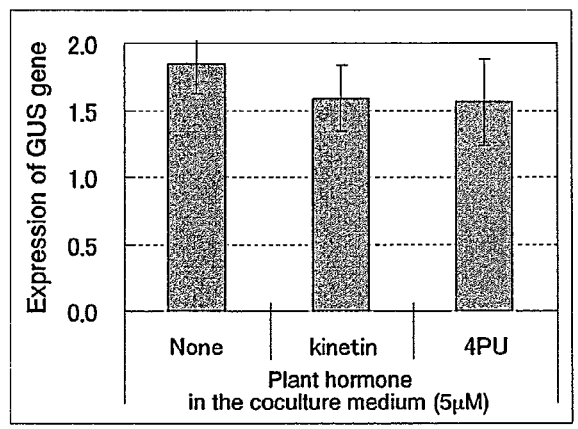
FIG. 4 is a graph showing the results of investigation of the effect of addition of a 5 µM plant hormone to the coculture medium on transformation efficiency. The three columns in FIG. 4 represent a test group where a plant hormone was not added, a test group where 5 µM kinetin was added, and a test group where 5 µM 4PU was added, from the left. The immature embryos were evaluated by expression of a GUS gene in individual immature embryos cultured in a resting medium for five days in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression). In each group, the evaluation was performed with 16 or 17 immature embryos, and the average value thereof was plotted on the vertical axis of FIG. 4. That is, the vertical axis in FIG. 4 represents the results of the efficiency of gene introduction for each test group by expression of the GUS gene.
Figure 5:
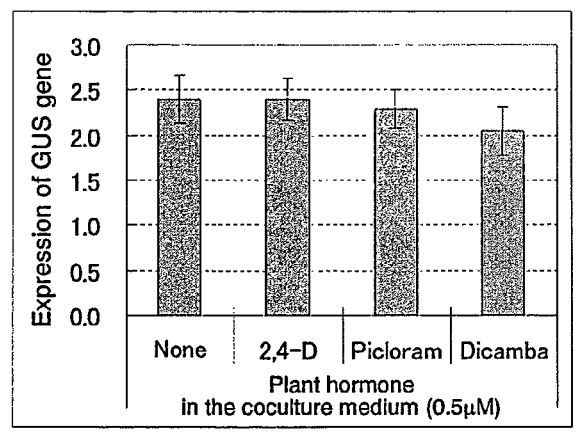
FIG. 5 is a graph showing the results of investigation of the effect of addition of a 0.5 µM plant hormone to the coculture medium on the transformation efficiency. The four columns in FIG. 5 represent a test group where a plant hormone was not added, a test group where 0.5 µM 2,4-D was added, a test group where 0.5 µM picloram was added, and a test group where 0.5 µM dicamba was added, from the left. The immature embryos were evaluated by expression of a GUS gene in individual immature embryos cultured in a resting medium for five days in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression). In each group, the evaluation was performed with 10 immature embryos, and the average value thereof was plotted on the vertical axis of FIG. 5. That is, the vertical axis in FIG. 5 represents the results of the efficiency of gene introduction for each test group by expression of the GUS gene.
Figure 6:
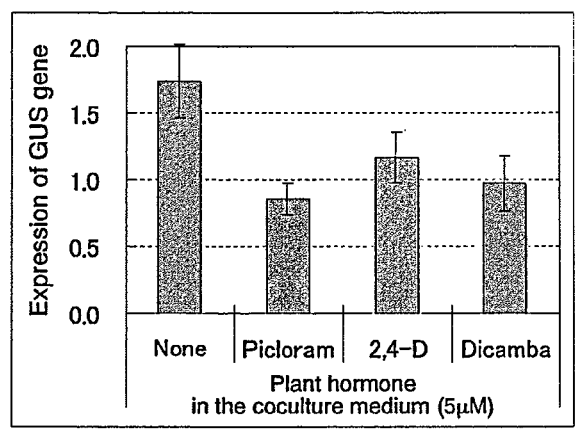
FIG. 6 is a graph showing the results of investigation of the effect of addition of a 5 µM plant hormone to the coculture medium on the transformation efficiency. The four columns in FIG. 6 represent a test group where a plant hormone was not added, a test group where 5 µM picloram was added, a test group where 5 µM 2,4-D was added, and a test group where 5 µM dicamba was added, from the left. The immature embryos were evaluated by expression of a GUS gene in individual immature embryos cultured in a resting medium for five days in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression). In each group, the evaluation was performed with 18 or 19 immature embryos, and the average value thereof was plotted on the vertical axis of FIG. 6. That is, the vertical axis in FIG. 6 represents the results of the efficiency of gene introduction for each test group by expression of the GUS gene.

A part of the immature embryos in each test group was harvested on the 5th day of the resting culture, and the GUS gene was expressed. The results are shown in FIGS. 4, 5, and 6. The vertical axis in each of FIGS. 4, 5, and 6 represents the average of GUS gene expression by each immature embryo evaluated in six grades: 4 (expressed in 75% or more of scutellum), 3 (expressed in 50% to 74% of scutellum), 2 (expressed in 25% to 49% of scutellum), 1 (expressed in 5% to 24% of scutellum), 0.5 (expressed in 1% to 4% of scutellum), and 0 (no expression), that is, efficiency of gene introduction shown by expression of the GUS gene.

As shown in FIG. 4, in the test groups of coculture medium containing 5 µM kinetin or 4PU, immature embryos expressing the GUS gene were obtained. The degrees of the expression were slightly lower than that of the immature embryos cultured in the coculture medium not containing plant hormones.

As shown in FIG. 5, the degrees of expression of the GUS gene in the immature embryos cultured in the coculture medium containing 0.5 µM 2,4-D, picloram, or dicamba were equivalent to or slightly lower than that of the immature embryos cultured in the coculture medium not containing plant hormones.

As shown in FIG. 6, in the test groups of culture medium containing 5 µM 2,4-D, picloram, or dicamba, immature embryos expressing the GUS gene were obtained. The degrees of the expression were slightly lower than that of the immature embryos cultured in the coculture medium not containing plant hormones.

These results reveal that in the method of the present invention, the efficiency of gene introduction in the case of the coculture medium containing cytokinin and a low concentration of an auxin is equivalent to or slightly lower than that in the coculture medium not containing plant hormones.

Thus, it is revealed that addition of a high concentration of an auxin to a medium decreases the efficiency of gene introduction compared to the medium not containing plant hormones.

Example 10

Effect of the Size of Immature Embryo on Production of Transformed Plant

Material and Method

An EHA105 (pIG121-PubiIubiBAR) vector was produced as in Example 7. Bread wheat (variety: Fielder) was cultivated in a greenhouse equipped with an air conditioner, and the immature embryos (size: 1.2 to 3.0 mm) of the bread wheat were aseptically collected on the 14th day after flowering and were washed once with an Inf liquid medium. Pretreatment (centrifugation at 7500 rpm for 10 min) was performed to enhance the efficiency of gene introduction in an Inf liquid medium. Agrobacterium strain EHA105 (pIG121-PubiIubiBAR) was suspended at about $1.0 \times 10^9$ cfu/mL in an Inf liquid medium containing 100 µM acetosyringone to prepare an inoculation source. The inoculation source was added to the immature embryos, and the mixture was stirred for 30 sec, followed by leaving to stand at room temperature for 5 min. The immature embryos inoculated with Agrobacterium were classified by size into test groups of 1.2 to 1.8 mm, 1.8 to 2.2 mm, and 2.2 to 3.0 mm, and the immature embryos in each group were placed onto a Co-Cul coculture medium containing 100 µM acetosyringone, 5 µM AgNO₃, and 5 µM CuSO₄ in such a manner that the scutellum faced upward, and were cocultured at 23° C. in the dark.

On the 2nd day from the beginning of the coculture, the radicles, germs, and embryonic axes were excised using a scalpel and tweezers. The immature embryos were placed onto a resting medium (the composition was the same as that described in Example 1), followed by cultivation at 25° C. in the dark for 5 days. Subsequently, the immature embryos were placed onto a primary selection medium that was a resting medium containing 5 mg/L of phosphinothricin (PPT), followed by cultivation under the same conditions for 2 weeks. Subsequently, the immature embryos were placed onto a secondary selection medium that was a resting medium containing 10 mg/L of PPT.

The immature embryos were cultured under the same conditions for 3 weeks, and were placed onto an LSZ medium containing 5 mg/L of PPT, followed by cultivation at 25° C. in the light for 2 weeks. Regenerated plants were placed onto an LSF medium containing 5 mg/L of PPT, followed by cultivation under the same conditions for 2 weeks. The plants having rooting were placed onto an LSF medium not containing hygromycin, followed by cultivation for 1 to 2 weeks. Then, a regenerated individual showing tremendous rooting was defined as a transformant, and the number thereof was investigated.

Results

Table 6 shows transformation efficiency in immature embryos in each group. In Table 6, each transformation efficiency (B)/(A) is shown in the rightmost column, wherein (A) represents the number of inoculated immature embryos and (B) represents the number of plant individuals showing PPT resistance.

In every test group, independent regenerated plants showing resistance to PPT were obtained from the inoculated immature embryos. In particular, for immature embryos having a size of 2.2 to 3.0 mm at the time of the inoculation, transformed plants were obtained from 70% or more of the inoculated immature embryos. Thus, it is revealed that transformation efficiency of the method of the present invention is significantly high.

TABLE 6

Results of transformation in immature embryos having different sizes

| Size of immature embryo at the time of inoculation (mm) | Number of immature embryos Inoculation (A) | Production of PPT resistant plant (B) | Transformation efficiency (B/A, %) |
|---|---|---|---|
| 1.2 to 1.8 | 22 | 1 | 4.5 |
| 1.9 to 2.2 | 28 | 15 | 53.6 |
| 2.3 to 3.0 | 28 | 20 | 71.4 |

The invention claimed is:

1. A method of gene introduction into a tissue of an immature embryo or mature seed isolated or harvested from a plant body of a *Triticum* plant, comprising the steps of:
   (i) coculture step by coculturing the tissue inoculated with *Agrobacterium*, in the presence of the *Agrobacterium*; and
   (ii) a step of [physically and/or chemically] damaging one or more portions selected from a radicle, a germ, and an embryonic axis of the tissue comprising excising one or more portions selected from the radicle, the germ, and the embryonic axis from the tissue simultaneous with and/or subsequent to the coculture step.

2. A method of producing a transformed *Triticum* plant, comprising the steps of:
   (i) coculture step by coculturing a tissue of an immature embryo or mature seed, which is isolated or harvested from a plant body of a *Triticum* plant, inoculated with *Agrobacterium*, in the presence of the *Agrobacterium*;
   (ii) a step of [physically and/or chemically] damaging one or more portions selected from a radicle, a germ, and an embryonic axis of the tissue comprising excising one or more portions selected from the radicle, the germ, and the embryonic axis from the tissue simultaneous with and/or subsequent to the coculture step;
   (iii) resting step by culturing the tissue on a resting medium; and
   (iv) a step of regenerating the tissue on a regeneration medium to produce the transformed *Triticum* plant.

3. The method according to claim 1, wherein the step of [physically and/or chemically] damaging one or more portions selected from a radicle, a germ, and an embryonic axis of the tissue comprising excising one or more portions selected from the radicle, the germ, and the embryonic axis from the tissue is performed simultaneous with the co culture step and/or within seven days from the beginning of the co culture step.

4. The method according to claim 1, wherein the step of [physically and/or chemically] damaging one or more portions selected from a radicle, a germ, and an embryonic axis of the tissue comprising excising one or more portions selected from the radicle, the germ, and the embryonic axis from the tissue is performed within one to three days from the beginning of the coculture step.

5. The method according to claim 1, wherein the coculture medium does not contain a plant growth regulator.

6. The method according to claim 1, the method further comprising at least one treatment for transformation efficiency enhancement selected from the group consisting of:
   a) centrifugation;
   b) addition of silver nitrate and/or copper sulfate to the coculture medium;
   c) thermal treatment;
   d) thermal treatment and centrifugation;
   e) pressurization;
   f) inoculation with *Agrobacterium* in the presence of a powder; and
   g) addition of cysteine to the coculture medium.

7. The method according to claim 1, the method further comprising the following a) and/or b) treatment for transformation efficiency enhancement:
   a) centrifugation;
   b) addition of silver nitrate and/or copper sulfate to the coculture medium.

8. The method according to claim 2, the method further comprising a step of selection with a selective drug between the resting step (iii) and the regeneration step (iv).

9. The method according to claim 2, wherein the resting medium (iii) and/or a selection medium for the step of selection with a selective drug contains a plant growth regulator.

10. The method according to claim 1, wherein the *Agrobacterium* is a bacterium selected from the group consisting of LBA4404, EHA101, EHA105, AGL1, and C58C1.

11. The method according to claim 1, wherein the *Triticum* plant is bread wheat (*Triticum aestivum*) or macaroni wheat (*Triticum durum*).

* * * * *

UNITED STATES PATENT AND TRADEMARK OFFICE
CERTIFICATE OF CORRECTION

| | | |
|---|---|---|
| PATENT NO. | : 8,884,101 B2 | Page 1 of 1 |
| APPLICATION NO. | : 13/387370 | |
| DATED | : November 11, 2014 | |
| INVENTOR(S) | : Yuji Ishida et al. | |

It is certified that error appears in the above-identified patent and that said Letters Patent is hereby corrected as shown below:

IN THE CLAIMS:

In claim 1, at column 37, line 23, delete "[physically and/or chemically]".

In claim 2, at column 37, line 35, delete "[physically and/or chemically]".

In claim 3, at column 37, line 46, delete "[physically and/or chemically]".

In claim 4, at column 37, line 54, delete "[physically and/or chemically]".

Signed and Sealed this
Fourteenth Day of April, 2015

Michelle K. Lee
*Director of the United States Patent and Trademark Office*